(12) United States Patent
Hikosaka et al.

(10) Patent No.: US 8,344,092 B2
(45) Date of Patent: Jan. 1, 2013

(54) METHOD FOR PRODUCING BISCHLOROFORMATE COMPOUND, POLYCARBONATE OLIGOMER HAVING SMALL NUMBER OF MONOMERS AND SOLUTION CONTAINING BISCHLOROFORMATE COMPOUND

(75) Inventors: Takaaki Hikosaka, Sodegaura (JP);
Hideyuki Miyamoto, Tokyo (JP);
Hiroichi Hokari, Aizuwakamatsu (JP);
Chikayuki Chiba, Aizuwakamatsu (JP);
Hitoshi Takemoto, Ageo (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 13/261,106

(22) PCT Filed: Jun. 25, 2010

(86) PCT No.: PCT/JP2010/060893
§ 371 (c)(1),
(2), (4) Date: Dec. 23, 2011

(87) PCT Pub. No.: WO2010/150888
PCT Pub. Date: Dec. 29, 2010

(65) Prior Publication Data
US 2012/0101292 A1    Apr. 26, 2012

(30) Foreign Application Priority Data

Jun. 26, 2009 (JP) .................... 2009-152988
Jun. 26, 2009 (JP) .................... 2009-152989

(51) Int. Cl.
*C08G 64/00* (2006.01)
*C08G 63/02* (2006.01)
(52) U.S. Cl. ......... 528/196; 558/269; 558/281; 528/198
(58) Field of Classification Search .................. 558/269, 558/281; 528/196, 198
See application file for complete search history.

(56) References Cited

U.S. PATENT DOCUMENTS

| 4,085,129 | A | 4/1978 | Semler et al. |
| 4,649,210 | A | 3/1987 | Kosky et al. |
| 7,297,754 | B2 | 11/2007 | Davis et al. |
| 2005/0176832 | A1 | 8/2005 | Tonkovich et al. |
| 2006/0293535 | A1 | 12/2006 | Davis et al. |

FOREIGN PATENT DOCUMENTS

| GB | 1 400 184 | 7/1975 |
| JP | 51-033897 A | 3/1976 |
| JP | 51-33897 B | 9/1976 |
| JP | 59-008256 B2 | 2/1984 |
| JP | 62-116544 A | 5/1987 |
| JP | 01-275631 A | 11/1989 |
| JP | 05-070583 A | 3/1993 |
| JP | 08-027068 A | 1/1996 |
| JP | 2003-210959 A | 7/2003 |
| JP | 2007-524681 A | 8/2007 |
| JP | 2008-543969 A | 12/2008 |

OTHER PUBLICATIONS

Brunelle et al,. "Preparation and Polymerization of Bisphenol A Cyclic Oligomeric Carbonates," Macromolecules, 1991, 24:3035-3044.

*Primary Examiner* — Terressa Boykin
(74) *Attorney, Agent, or Firm* — Foley & Lardner LLP

(57) ABSTRACT

A dihydric phenol compound represented by the following formula (2), a phosgene compound, and an aliphatic tertiary amine are mixed together using a hydrophobic organic solvent to produce bischloroformate that is represented by the following formula (1) and has an average number of repeating units (n) of 1.99 or less.

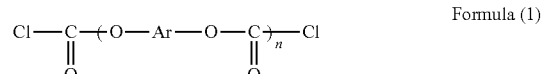

Formula (1)

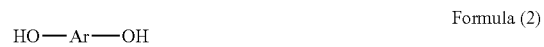

Formula (2)

In the formulae (1) and (2), Ar is a divalent aromatic group.

12 Claims, 4 Drawing Sheets

METHOD FOR PRODUCING BISCHLOROFORMATE COMPOUND, POLYCARBONATE OLIGOMER HAVING SMALL NUMBER OF MONOMERS AND SOLUTION CONTAINING BISCHLOROFORMATE COMPOUND

CROSS-REFERENCE TO RELATED APPLICATIONS

This application is a National Stage application of PCT/JP2010/060893, filed Jun. 25, 2010, which claims priority from Japanese applications JP 2009-152988, filed Jun. 26, 2009, and JP 2009-152989, filed Jun. 26, 2009.

TECHNICAL FIELD

The present invention relates to a bischloroformate compound production method, a polycarbonate oligomer having a small number of repeating units and a bischloroformate-compound-containing solution.

BACKGROUND ART

There has been conventionally known phenols such as phenol, biphenol having two phenols directly bonded to each other, and bisphenol having two phenols bonded to each other via a bonding group. It has been suggested that phenolic hydroxyl groups of the above phenols are chloroformatized for synthesis of chloroformate compounds (see, for example, Patent Literatures 1 to 4 and Non-patent Literature 1).

Patent Literature 1 discloses that p-nitrophenol and phosgene are reacted together using toluene as a solvent under the presence of N,N-diethylaniline to prepare p-nitrophenylchloroformate.

Patent Literature 2 discloses that biphenol and phosgene are reacted together using tetrahydrofuran (THF) as a solvent under the presence of N,N-dimethylaniline to prepare a bischloroformate, i.e., biphenolbischloroformate.

Patent Literature 3 discloses a production method of a haloformate compound low in the hydrolysis level of a halocarbonyl compound. Patent Literature 3 also discloses a production method in which a mixture and an aqueous sodium hydroxide are introduced into a tubular reactor to obtain a chloroformate compound, the mixture being obtained by stirring a suspension made from bisphenol A and dichloromethane after supplying phosgene thereto.

Patent Literature 4 discloses a bischloroformate compound obtained by bonding two phenols via an ester bond. It is also disclosed that the bischloroformate compound of Patent Literature 4 can be obtained by mixing 4-hydroxybenzoic acid-(4'-hydroxyphenyl)ester, phosgene and dimethylaniline.

Non-patent Literature 1 discloses a method of producing a bischloroformate compound using bisphenol A as an ingredient under the presence of diethylaniline.

Citation List
Patent Literatures
  Patent Literature 1 JP-B-59-8256
  Patent Literature 2 JP-A-5-70583
  Patent Literature 3 JP-A-8-27068
  Patent Literature 4 JP-A-1-275631
Non-Patent Literature
  Non-Patent Literature 1 Macromolecules Vol.24 3035-3044 (1991)

SUMMARY OF THE INVENTION

Problems to be Solved by the Invention

Patent Literature 1 is silent as to a method of bischloroformatizing a dihydric phenol compound such as biphenol and bisphenol.

According to the technique disclosed in Patent Literature 2, for producing a bischloroformate compound, a reaction liquid is poured in ice water to precipitate crystals. Additionally, recrystallization is performed using acetone. Since it takes time to produce the bischloroformate compound as described above, productivity is likely to be lowered.

The production method disclosed in Patent Literature 3 employs an interface method using both liquid phase and organic phase. According to this production method, for suppressing the hydrolysis level, a particularly preferable range of pH is set narrow, such as approximately from 9 to 11. Thus, pH needs to be slightly adjusted in producing, which adversely affects productivity. According to the technique disclosed in Patent Literature 3, since the suspension is introduced into the reactor as disclosed therein, for instance, the reactor is likely to be clogged to impair handleability. Thus, productivity is likely to be lowered.

The bischloroformate compound disclosed in Patent Literature 4 uses a highly acidic reaction system, which is likely to cause esterolysis or to cause transesterification with the 4-hydroxybenzoic acid-(4'-hydroxyphenyl)ester (an ingredient). Thus, a purifying process such as recrystallization is required to remove a by-product, which adversely affects productivity.

The method disclosed in Non-patent Literature 1 uses an aromatic tertiary amine, so that a bischloroformate reaction solution is unintentionally colored. Thus, a polymer produced using this bischloroformate compound is likely to have an unfavorable color. Thus, the bischloroformate compound may need to be recrystallized to be purified, so that productivity is likely to be lowered.

An object of the invention is to provide a bischloroformate compound production method, a polycarbonate oligomer having a small number of repeating units and a bischloroformate-compound-containing solution, which contribute to improvement in productivity.

Means for Solving the Problems

According to an aspect of the invention, a bischloroformate compound production method of producing a bischloroformate compound represented by a formula (1) below, the method includes: mixing a dihydric phenol compound represented by a formula (2) below, a phosgene compound, and an aliphatic tertiary amine together using a hydrophobic organic solvent to produce bischloroformate represented by the formula (1), the bischloroformate having an average number of repeating units (n) of 1.99 or less, the average number of repeating units (n) being calculated by an equation (1) below.

Formula 1

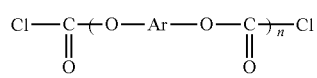

Formula (1)

Formula 2

Formula (2)

In the formulae (1) and (2), Ar is a divalent aromatic group.

Average Number of Repeating Units $(n)=1+(Mav-M1)/M2$  Equation (1)

In the Equation (1), Mav is $(2\times1000/(CF\ value))$, M2 is (M1−98.92), M1 is a molecular weight of the bischloroformate compound when n=1 in the formula (1), the CF value (N/kg) is (CF number/concentration), the CF number (N) is a chlorine molecule number of the bischloroformate compound represented by the formula (1) contained in a 1 L reaction solution, and the concentration (kg/L) is calculated from an amount of a solid resulting from condensation of the 1 L reaction solution. 98.92 is a total atomic weight of two chlorine atoms, one oxygen atom and one carbon atom that exist outside n repeating units in the formula (1).

The above aspect is exemplified by first and second exemplary embodiments. Specifically, when being mixed with the aliphatic tertiary amine, the dihydric phenol compound represented by the formula (1) provides a salt or an aggregate in the hydrophobic organic solvent, and thus becomes a homogeneous solution or a dispersion solution. The dihydric phenol compound existing in the homogeneous solution or dispersion solution is favorably reacted with the phosgene compound, thereby providing a monomer-like bischloroformate compound represented by the formula (1) with 1.99 or less repeating units.

An amine hydrochloride generated in the reaction solution can be easily extracted through liquid separation by adding water thereto. Since the hydrophobic organic solvent is used as a solvent, unlike when using a hydrophilic solvent, liquid separation can be performed by directly adding water, so that a purifying process can be facilitated. Since it is possible to provide monomer-like bischloroformate with 1.99 or less repeating units, a purifying process such as recrystallization can be omitted.

Since water does not exist in the reaction system between the phosgene compound and the dihydric phenol compound, hydrolysis of the generated acid chloride hardly occurs.

In the bischloroformate compound according to the above aspect, unlike the bischloroformate with an ester bond disclosed in Patent Literature 4, esterolysis or transesterification with the dihydric phenol compound (an ingredient) does not occur in the reaction system.

Using the aliphatic tertiary amine, unlike using an aromatic tertiary amine, prevents the reaction solution from being unintentionally colored, so that the resulting bischloroformate compound can have a favorable color. Thus, a special purifying process such as recrystallization is not required, so that production efficiency can be improved without lowering yield.

Since aliphatic tertiary amines are relatively cheap as compared with aromatic tertiary amines, the above arrangement also contributes to a reduction in production costs.

A more monomer-like bischloroformate compound can be provided in a simple method as described above, so that productivity can be improved.

In the above aspect, the bischloroformate compound represented by the formula (1) is a bischloroformate compound represented by one of formulae (3) and (4) below, and the dihydric phenol compound represented by the formula (2) is one of a biphenol compound represented by a formula (5) below and a bisphenol compound represented by a formula (6) below.

Formula 3

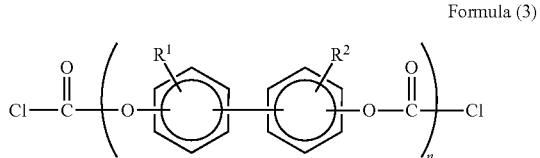

Formula (3)

Formula 4

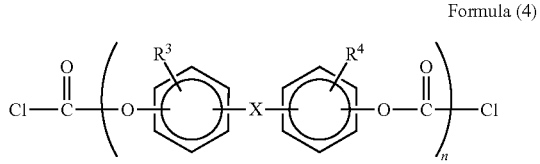

Formula (4)

Formula 5

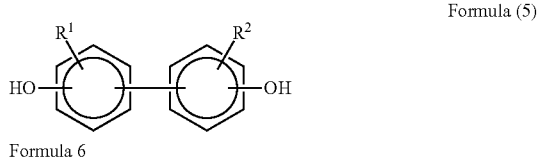

Formula (5)

Formula 6

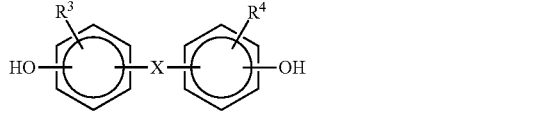

Formula (6)

In the formulae (3) to (6), $R^1$ and $R^2$ each independently represent a hydrogen atom, an alkyl group having 1 to 12 carbon atoms, or a substituted or unsubstituted aryl group having 6 to 12 carbon atoms, $R^3$ and $R^4$ each independently represent a hydrogen atom, an alkyl group having 1 to 12 carbon atoms, an aryl group having 6 to 12 carbon atoms, or a halogen atom, and X is 9,9-fluorenylidene group, a divalent adamantyl group, or a linking group represented by one of formulae (7a) and (7b) below.

Formula 7

Formula (7a)

In the formula (7a), $R^5$ and $R^6$ each independently a hydrogen atom, a trifluoromethyl group, an alkyl group having 1 to 12 carbon atoms, or an aryl group having 6 to 12 carbon atoms. $R^5$ and $R^6$ may be combined with each other to provide a cycloalkylidene group having 4 to 12 carbon atoms.

Formula 8

Formula (7b)

In the formula (7b), each of a plurality of R is a hydrogen atom or an alkyl group having 1 to 3 carbon atoms, and at least one, preferably three, of the plurality of R is an alkyl group having 1 to 3 carbon atoms.
Substituents corresponding to $R^1$, $R^2$, $R^3$ and $R^4$ may be plurally combined with one benzene ring, and the combined substituents may be the same or different.

For instance, in the first exemplary embodiment, the method further includes: suspending or dissolving the dihydric phenol compound represented by the formula (2) in the hydrophobic organic solvent; introducing the phosgene compound into a resulting suspension or solution; and dropping the aliphatic tertiary amine in a mixture obtained by the introducing of the phosgene compound, the aliphatic tertiary amine being diluted with the hydrophobic organic solvent.

With the above arrangement, the bischloroformate compound represented by the formula (1) can be provided in a good yield.

For instance, in the second exemplary embodiment, the method further includes: suspending or dissolving the dihydric phenol compound represented by the formula (2) in the hydrophobic organic solvent; introducing the aliphatic tertiary amine into a resulting suspension or solution; and dropping the resulting suspension or solution, in which the aliphatic tertiary amine is introduced, in the phosgene compound being diluted with the hydrophobic organic solvent.

With the above arrangement, the bischloroformate compound of the formula (1) can be provided in a good yield. Additionally, when being mixed with the aliphatic tertiary amine, the dihydric phenol compound represented by the formula (2) is dissolved in the hydrophobic organic solvent, thereby providing a homogeneous solution or reducing slurry concentration. Such a homogeneous solution or a heterogeneous solution with a reduced slurry concentration is easy to handle, so that, for instance, the solution can be easily dropped.

In the above aspect, a used amount of the aliphatic tertiary amine is 1.1 equivalent weight or less relative to a hydroxyl group in the dihydric phenol compound represented by the formula (2).

When the aliphatic tertiary amine such as triethylamine is used to cause a bischloroformatizing reaction of the dihydric phenol compound represented by the formula (2), a part of the amine is likely to be unintentionally reacted with a chloroformate group or a phosgene compound depending on reaction conditions, which may result in a side reaction to generate a carbamate group (—O—CO—N($C_2H_5$)$_2$). The substitution reaction of the carbamate group does not further proceed, so that the carbamate group functions as a terminal terminator. Thus, when the ratio of the carbamate group to all terminal functional groups in the reactant exceeds 10 mol %, it is difficult to provide a polymer having a predetermined molecular weight or more.

It has been revealed that such a side reaction is caused when the amount of amine is excessive to the hydroxyl group.

In view of the above, in the above aspect, a specific amount of the aliphatic tertiary amine is used with respect to the hydroxyl group to reduce generation of the carbamate group.

According to another aspect of the invention, a polycarbonate oligomer having a small number of repeating units and being produced using the bischloroformate compound that is obtained in the above method and is represented by the formula (1), the polycarbonate oligomer includes a nitrogen-containing terminal group at a ratio of 10 mol % of all terminal groups or less or includes no nitrogen-containing terminal group.

An example of the nitrogen-containing terminal group is the above carbamate group.

With the above arrangement, since the nitrogen-containing terminal group is contained at the specific ratio or less, a high polymer can be favorably produced using the polycarbonate oligomer having a small number of repeating units according to the invention.

According to another aspect of the invention, a bischloroformate-compound-containing solution includes the bischloroformate compound produced in the above method.

With the above arrangement, the bischloroformate-compound-containing solution is usable as ingredients for a variety of polymers such as polycarbonate (PC).

The solvent used for the bischloroformate-compound-containing solution is preferably a hydrophobic solvent incompatible with water, an inert solvent unreactive with bischloroformate compounds, or the like.

According to another aspect of the invention, a bischloroformate compound production method of producing a bischloroformate compound represented by a formula (1) below, the method includes: continuously reacting a solution, in which a dihydric phenol compound represented by a formula (2) below is dissolved in an alkali aqueous solution, with a phosgene compound in a fine flow path in a micrometer order under presence of an inert organic solvent to obtain bischloroformate having an average number of repeating units (n) of 1.99 or less, the average number of repeating units (n) being calculated by an equation (1) below.

Formula 9

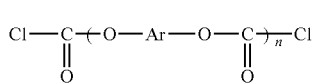

Formula (1)

Formula 10

Formula (2)

In the formulae (1) and (2), Ar is a divalent aromatic group.

Average Number of Repeating Units $(n)=1+(Mav-M1)/M2$  Equation (1)

In the Equation (1), Mav is (2×1000/(CF value)), M2 is (M1−98.92), M1 is a molecular weight of the bischloroformate compound when n=1 in the formula (1), the CF value (N/kg) is (CF number/concentration), the CF number (N) is a chlorine molecule number of the bischloroformate compound represented by the formula (1) contained in a 1 L reaction solution, and the concentration (kg/L) is calculated from an amount of a solid resulting from condensation of the 1 L reaction solution. 98.92 is a total atomic weight of the two chlorine atoms, the one oxygen atom and the one carbon atom outside n repeating units in the formula (1)

In the above aspect of the invention, as components to be introduced into the fine flow path, the following two kinds of solutions are preferable: a solution obtained by dissolving the dihydric phenol compound represented by the formula (2) in an alkali aqueous solution; and a solution obtained by dissolving the phosgene compound in an inert solvent. With this arrangement, since both of the above components, each being in the form of solution, are introduced into the fine flow path, the reaction therebetween can uniformly and rapidly proceed in a reactor having the fine flow path without clogging the introduction line. Thus, it is possible to efficiently produce the bischloroformate compound having an average number of repeating units (n) of 1.99 or less.

In the above aspect of the invention, a bischloroformatizing reaction instantly proceeds in the fine flow path. In order to instantly mix the material solutions to prevent generation of a bischloroformate compound having an average number of repeating units (n) of 2 or more, a fine flow path in a micrometer order is required. In the above aspect of the invention, it is important to instantly mix the material solutions, so that it is not necessary for the material solutions to be retained in the fine flow path for an extended time. It is sufficient for the material solutions to be retained for, for instance, approximately 0.01 seconds to several seconds.

In the above aspect of the invention, it is important to instantly mix the material solutions. As reactors with flow paths fine enough for instant mixing, a micromixer and a mixroreactor as described in Examples hereinblelow are commercially available. Since many of such commercially available reactors have flow paths shaped to enable instant mixing, the inner diameter of the fine flow path cannot be unambiguously determined herein. Thus, an expression "micrometer order" is used herein.

Although the inner diameter of the reactor cannot be unambiguously determined as described above, the fine flow path, which has a minimum number of mixing members for mixing two solutions therein, is only required to have a major axis of 1 mm or shorter (i.e., in a micrometer order). Supposing that mixing members are juxtaposed with one another in a pipe to form a plurality of fine flow paths, the major axis of the pipe is likely to exceed 1 mm. The major axis of each fine flow path preferably falls within a range from 10 μm to 1000 μm, more preferably from 10 μm to 700 μm. When the major axis is longer than 1000 μm, it may take more time to complete the mixing, so that a bischloroformate compound having an average number of repeating units (n) of 2 or more is likely to be generated. There is no lower limit of the major axis. However, when the major axis is shorter than 10 μm, a mixing portion may be difficult to process, and a flow rate may be reduced to lower productivity.

In the above aspect, in the fine flow path, a linear velocity of a mixture of the dihydric phenol compound represented by the formula (2) and the phosgene compound preferably falls within a range from 0.2 m/sec to 50 m/sec, more preferably, from 0.2 m/sec to 30 m/sec.

With the above arrangement, since the solution containing the dihydric phenol compound represented by the formula (2) and the phosgene solution are mixed together to provide a specific linear velocity, mixing efficiency can be improved to provide the bischloroformate compound of the formula (1) in a good yield.

In the above aspect, in the fine flow path, a used amount of the phosgene compound preferably falls within a range from 0.95 to 10 equivalent weight relative to a hydroxyl group in the dihydric phenol compound represented by the formula (2), more preferably 1.0 to 3.0 equivalent weight.

With the above arrangement, since the dihydric phenol compound of the formula (2) is reacted with the phosgene compound at a specific ratio, it is possible to favorably provide a monomer-like bischloroformate compound having an average number of repeating units (n) of 1.99 or less.

DESCRIPTION OF EXEMPLARY EMBODIMENTS

Figure 1:
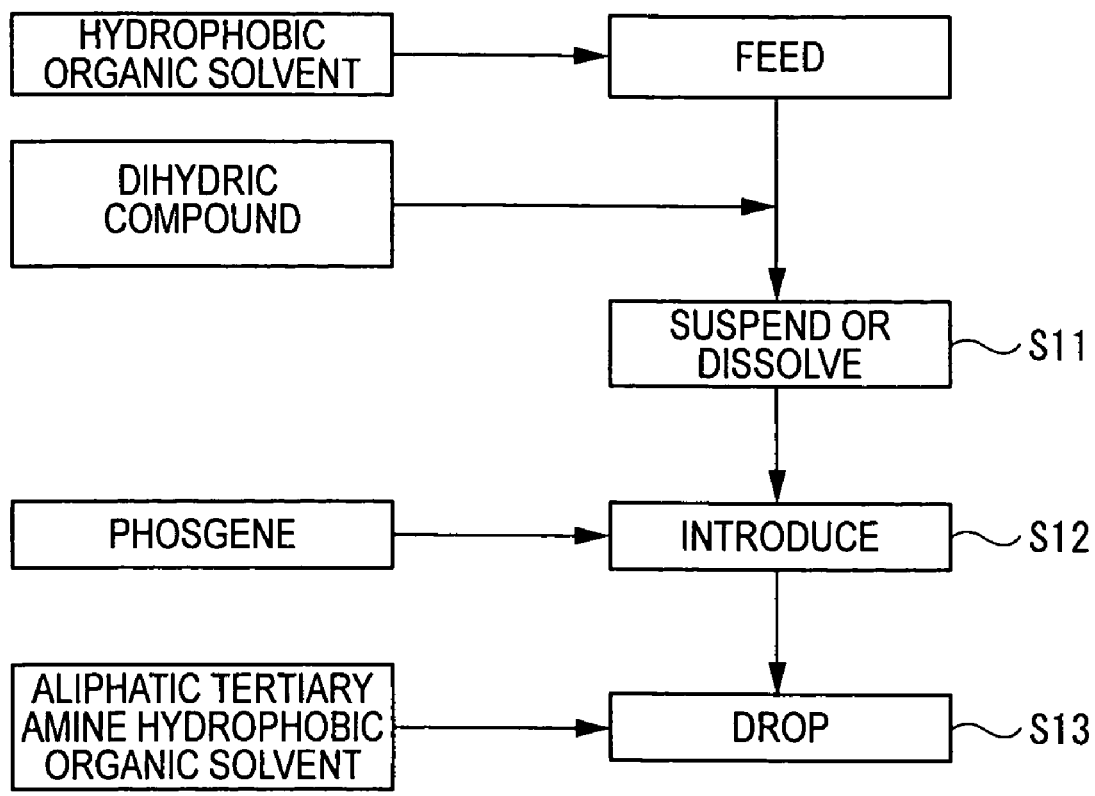
FIG. 1 is a flow chart showing a bischloroformate compound production method according to a first exemplary embodiment of the invention.

Description will be made below on a bischloroformate compound production method according to each of first, second and third exemplary embodiments of the invention.

First Exemplary Embodiment

A bischloroformate compound production method according to the first exemplary embodiment is intended to produce a bischloroformate compound represented by the following formula (1). Specifically, the production method includes mixing a dihydric phenol compound represented by the following formula (2), a phosgene compound, and an aliphatic tertiary amine together using a hydrophobic organic solvent to produce the bischloroformate compound represented by the formula (1), the bischloroformate having an average number of repeating units (n) of 1.99 or less, the average number of repeating units (n) being calculated by the following equation (1).

Formula 11

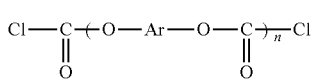

Formula (1)

Formula 12

$$HO-Ar-OH$$

Formula (2)

In the formulae (1) and (2), Ar is a divalent aromatic group.

Preferably, the compound represented by the formula (1) is a bischloroformate compound represented by the following formula (3) or (4), and the dihydric phenol compound represented by the formula (2) is a biphenol compound represented by the following formula (5) or a bisphenol compound represented by the following formula (6).

Formula 13

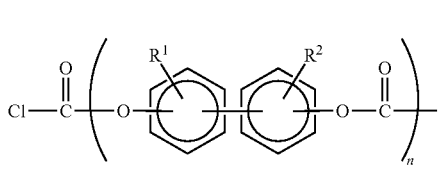

Formula (3)

Formula 14

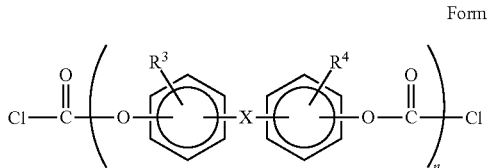

Formula (4)

Formula 15

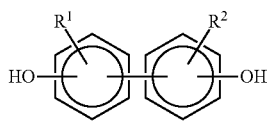

Formula (5)

Formula 16

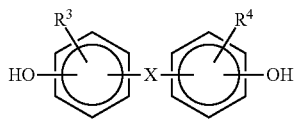

Formula (6)

In the formulae (3) to (6), $R^1$ and $R^2$ each independently represent a hydrogen atom, an alkyl group having 1 to 12 carbon atoms, or a substituted or unsubstituted aryl group having 6 to 12 carbon atoms, $R^3$ and $R^4$ each independently represent a hydrogen atom, an alkyl group having 1 to 12 carbon atoms, an aryl group having 6 to 12 carbon atoms, or a halogen atom, and X is 9,9-fluorenylidene group, a divalent adamantyl group, or a linking group represented by either of the following formulae (7a) and (7b).

Formula 17

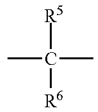

Formula (7a)

In the above formula, $R^5$ and $R^6$ each independently a hydrogen atom, a trifluoromethyl group, an alkyl group having 1 to 12 carbon atoms, or an aryl group having 6 to 12 carbon atoms. $R^5$ and $R^6$ may be combined with each other to provide a cycloalkylidene group having 4 to 12 carbon atoms.

Formula 18

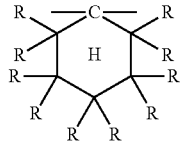

Formula (7b)

In the above formula, each of a plurality of R is a hydrogen atom or an alkyl group having 1 to 3 carbon atoms, and at least one, preferably three, of the plurality of R is an alkyl group having 1 to 3 carbon atoms.

It should be noted that substituents corresponding to $R^1$, $R^2$, $R^3$ and $R^4$ may be plurally combined with one benzene ring, and the combined substituents may be the same or different.

The bischloroformate compound represented by the formula (1) is a compound produced by chloroformatizing the two phenolic hydroxyl groups of the dihydric phenol compound represented by the formula (2). Examples of the dihydric phenol compound represented by the formula (2) include the biphenol compound represented by the formula (5) and the bisphenol compound represented by the formula (6). In addition, the dihydric phenol compound may be a dihydric phenol compound having two carbon atoms of a part of a benzene ring or a naphthalene ring being substituted with OH groups. Examples of such a compound include 2,7-naphthalenediol, 2,6-naphthalenediol, 1,4-naphthalenediol and 1,5-naphthalenediol.

Examples of the biphenol compound represented by the formula (5) include 4,4'-biphenol, biphenol, 3,3',5-trimethyl-4,4'-biphenol, 3-propyl-4,4'-biphenol, 3,3',5,5'-tetramethyl-4,4'-biphenol, 3,3'-diphenyl-4,4'-biphenol, 3,3'-dibutyl-4,4'-biphenol, and 3,3'-difluoro-4,4'-dihydroxyphenyl. Among the above, 4,4'-biphenol is preferable because it provides a less colored PC copolymer. One of the above may be singularly used or, alternatively, two or more may be used in combination.

Examples of the bisphenol compound represented by the formula (6) include 1,1-bis(3-methyl-4-hydroxyphenyl)ethane, 9,9-bis(3-phenyl-4-hydroxyphenyl)fluorene, bis(4-hydroxyphenyl)methane, 1,1-bis(4-hydroxyphenyl)ethane, 1,2-bis(4-hydroxyphenyl)ethane, 2,2-bis(4-hydroxyphenyl)propane, 2,2-bis(3-methyl-4-hydroxyphenyl)butane, 2,2-bis(4-hydroxyphenyl)butane, 2,2-bis(4-hydroxyphenyl)octane, 4,4-bis(4-hydroxyphenyl)heptane, 1,1-bis(4-hydroxyphenyl)-1,1-diphenylmethane, 1,1-bis(4-hydroxyphenyl)-1-phenylethane, 1,1-bis(4-hydroxyphenyl)-1-phenylmethane, 1,1-bis(4-hydroxyphenyl)cyclopentane, 1,1-bis(3-methyl-4-hydroxyphenyl)cyclopentane, 1,1-bis(4-hydroxyphenyl)cyclohexane, 2,2-bis(3-methyl-4-hydroxyphenyl)propane, 2,2-bis(3-phenyl-4-hydroxyphenyl)propane, 2,2-bis(4-hydroxyphenyl)adamantane, 2,2-bis(3-methyl-4-hydroxyphenyl)adamantane, 1,3-bis(4-hydroxyphenyl)adamantane, 1,3-bis(3-methyl-4-hydroxyphenyl)adamantane, 2-(3-methyl-4-hydroxyphenyl)-2-(4-hydroxyphenyl)-1-phenylethane, bis(3-methyl-4-hydroxyphenyl)methane, 1,1-bis(3-methyl-4-hydroxyphenyl)cyclohexane, 2,2-bis(2-methyl-4-hydroxyphenyl)propane, 1,1-bis(2-butyl-4-hydroxy-5-methylphenyl)butane, 1,1-bis(2-tert-butyl-4-hydroxy-5-methylphenyl)propane, 1,1-bis(2-tert-butyl-4-hydroxy-5-methylphenyl)butane, 1,1-bis(2-tert-butyl-4-hydroxy-5-methylphenyl)isobutene, 1,1-bis(2-tert-butyl-4-hydroxy-5-methylphenyl)heptane, 1,1-bis(2-tert-butyl-4-hydroxy-5-methylphenyl)-1-phenylmethane, 1,1-bis(2-tert-amyl-4-hydroxy-5-methylphenyl)butane, bis(3-chloro-4-hydroxyphenyl)methane, bis(3,5-dibromo-4-hydroxyphenyl)methane, 2,2-bis(3-chloro-4-hydroxyphenyl)propane, 2,2-bis(3-fluoro-4-hydroxyphenyl)propane, 2,2-bis(3-bromo-4-hydroxyphenyl)propane, 2,2-bis(3,5-difluoro-4-hydroxyphenyl)propane, 2,2-bis(3,5-dichloro-4-hydroxyphenyl)propane, 2,2-bis(3,5-dibromo-4-hydroxyphenyl)propane, 2,2-bis(3-bromo-4-hydroxy-5-chlorophenyl)propane, 2,2-bis(3,5-dichloro-4-hydroxyphenyl-butane, 2,2-bis(3,5-dibromo-4-hydroxyphenyl)butane, 1-phenyl-1,1-bis(3-fluoror-4-hydroxyphenyl)ethane, 1,1-bis(3-cyclohexyl-4-hydroxyphenyl)cyclohexane, 2,2-bis(4-hydroxyphenyl)hexafluoropropane, 1,1-bis(3-phenyl-4-hydroxyphenyl)cyclohexane, 4,4'-(3,3,5-trimethylcyclohexylidene)diphenol, 4,4'-[1,4-phenylenebis(1-methylethylidene)]bisphenol, 4,4'-[1,3-phenylenebis(1-methylethylidene)]bisphenol, 9,9-bis(4-hydroxyphenyl)fluorene, and 9,9-bis(4-hydroxy-3-methylphenyl)fluorene. One of the above bisphenol compounds may be singularly used or, alternatively, two or more may be used in combination. Additionally, three or more phenols may be used to provide a branched structure.

Among the above bisphenol compounds, preferred are 1,1-bis(4-hydroxyphenyl)ethane, 2,2-bis(4-hydroxyphenyl)butane, 2,2-bis(4-hydroxyphenyl)propane, 1,1-bis(4-hydroxyphenyl)-1,1-diphenylmethane, 1,1-bis(4-hydroxyphenyl)-1-phenylethane, 1,1-bis(4-hydroxyphenyl)cyclohexane, 2,2-bis(3-methyl-4-hydroxyphenyl)propane, 1,1-bis(3-methyl-4-hydroxyphenyl)cyclohexane, 1,1-bis(3-methyl-4-hydroxyphenyl)cyclopentane, 2,2-bis(3-phenyl-4-hydroxyphenyl)propane, 4,4'-(3,3,5-trimethylcyclohexylidene)diphenol, 4,4'-[1,4-phenylenebis(1-methylethylidene)]bisphenol, 4,4'-[1,3-phenylenebis(1-methylethylidene)]bisphenol, 9,9-bis(4-hydroxyphenyl)fluorene, and 9,9-bis(4-hydroxy-3-methylphenyl)fluorene.

Among the above, more preferred are 1,1-bis(4-hydroxyphenyl)ethane, 2,2-bis(4-hydroxyphenyl)butane, 2,2-bis(4-hydroxyphenyl)propane, 1,1-bis(4-hydroxyphenyl)-1-phenylethane, 1,1-bis(4-hydroxyphenyl)cyclohexane, 2,2-bis(3-methyl-4-hydroxyphenyl)propane, 1,1-bis(3-methyl-4-hydroxyphenyl)cyclohexane, 1,1-bis(3-methyl-4-hydroxyphenyl)cyclopentane, 2,2-bis(3-phenyl-4-hydroxyphenyl)propane, 4,4'-(3,3,5-trimethylcyclohexylidene)diphenol, and 9,9-bis(4-hydroxy-3-methylphenyl)fluorene.

$$\text{Average Number of Repeating Units } (n) = 1 + (Mav - M1)/M2 \quad \text{Equation (1)}$$

In the equation (1), Mav is $(2 \times 1000/(\text{CF value}))$, M2 is $(M1-98.92)$, M1 is a molecular weight of the bischloroformate compound when n=1 in the formula (1), the CF value (N/kg) is (CF number/concentration), the CF number (N) is a chlorine molecule number of the bischloroformate compound of the formula (1) contained in a 1 L reaction solution, and the concentration (kg/L) is calculated from the amount of a solid resulting from condensation of the 1 L reaction solution. 98.92 is the total atomic weight of the two chlorine atoms, the one oxygen atom and the one carbon atom outside n repeating units in the formula (1).

Usable as the hydrophobic organic solvent are, for instance, aromatic hydrocarbons such as toluene, xylene and benzene, aliphatic hydrocarbons such as pentane, heptane, hexane, octane, isooctane, cyclobutane, cyclopentane, cyclohexane and 1,3-dimethylcyclohexane, halogenated hydrocarbons such as dichloromethane and chloroform, ketones such as methylisobutylketone, methylethylketone and cyclohexanon, and ethers such as diethylether, diisopropylether and dibutylether. One of the above may be singularly used or, alternatively, two or more may be used in combination.

The hydrophobic organic solvent is not particularly limited in used amount, but is preferably used in such a manner that the concentration of the dihydric phenol compound represented by the formula (2) (an ingredient), falls within a range from 30 (g/L) to 420 (g/L), more preferably from 60 (g/L) to 250 (g/L).

Examples of the phosgene compound include phosgene, diphosgene and triphosgene, one of which may be singularly used or, alternatively, two or more may be used in combination.

The used amount of the phosgene compound is not particularly limited, but is preferably 0.95 equivalent weight or more relative to a hydroxyl group in the dihydric phenol compound represented by the formula (2) (an ingredient). Using a large amount of the phosgene compound is economically disadvantageous, so that the used amount preferably falls within a range from 0.97 to 1.60 equivalent weight.

Usable as the aliphatic tertiary amine are trialkylamines such as triethylamine, trimethylamine and tripropylamine, one of which may be singularly used or, alternatively, two or more may be used in combination.

The used amount of the aliphatic tertiary amine is not particularly limited, but is preferably 1.1 equivalent weight or less relative to a hydroxyl group in the dihydric phenol compound represented by the formula (2) (an ingredient).

Using a large amount of the aliphatic tertiary amine is likely to lead to generation of a by-product containing the carbamate group ($-O-CO-N(C_2H_5)_2$) as described above.

When the ratio of the carbamate group to all terminal functional groups in the reactant exceeds 10 mol %, a high polymer is unlikely to be obtained even using the dihydric phenol compound represented by the formula (2) because the substitution reaction of the carbamate group does not further proceed. In view of the above, the ratio of the carbamate group in the reactant is preferably 10 mol % or less.

Using a large amount of the aliphatic tertiary amine is economically disadvantageous and thus not preferable. In view of the above, the used amount of the aliphatic tertiary amine is preferably 1.1 equivalent weight or less, more preferably 0.95 equivalent weight to 1.02 equivalent weight.

The bischloroformate compound production method according to the first exemplary embodiment will be described below in detail. As shown in FIG. 1, the production method includes a suspending or dissolving step that suspends or dissolves the dihydric phenol compound represented by the formula (2) in a hydrophobic organic solvent (S11), a phosgene introducing step that introduces phosgene into the resulting suspension or solution (S12), and a dropping step that drops an aliphatic tertiary amine in the mixture obtained by the phosgene introducing step, the aliphatic tertiary amine being diluted with a hydrophobic organic solvent (S13).

In the suspending or dissolving step, the hydrophobic organic solvent and the bisphenol compound are mixed together to prepare a suspension or solution. In the phosgene introducing step, phosgene is introduced into the suspension or solution obtained by the suspending step or dissolving step. Subsequently, in the dropping step, the aliphatic tertiary amine, which has been diluted with the hydrophobic organic solvent, is dropped in the mixture of the suspension or solution and the phosgene to produce the bischloroformate compound represented by the formula (1).

The resulting reaction solution is added with water or acid aqueous solution to wash an organic layer so that an amine salt is extracted in a water layer for purification.

The water used therefor may be pure water, and the acid aqueous solution may be an inorganic acid such as hydrochloric acid or an organic acid such as acetic acid. In addition, salt aqueous solutions such as low-concentration basic aqueous solution and sodium chloride solution are also usable. The pH of the water layer is adjusted in consideration of a distribution coefficient between the water layer and organic layer of the aliphatic tertiary amine used for producing the bischloroformate compound of the formula (1). Specifically, for efficiently moving the amine salt to the water layer, the pH is preferably 5 or less, more preferably 4 or less, further more preferably 3 or less, the most preferably in a range from 1 to 3. With a pH of 5 or less, it is possible to favorably extract the amine salt in the water layer to suppress the aliphatic tertiary amine from being remained in the organic layer. A pH more than 7 is not preferable because the aliphatic tertiary amine is more likely to be remained in the organic layer.

If necessary, in addition to washing with water or acid aqueous solution, the organic layer is preferably washed once or a plurality of times with water to remove impurities generated during producing the bischloroformate compound of the formula (1) and an unreacted residual chemical species such as salt, carbamate compound and phenol compound. For washing the organic layer once or a plurality of times, any one of acid aqueous solution, basic aqueous solution and salt aqueous solution is usable in place of water. Even in this case, the washing solution is likewise preferably selected in consideration of a distribution coefficient of the residual impurities and the like (water/organic layer).

The acid aqueous solution is not limited to hydrochloric acid, but a variety of acids may be usable.

Specifically, the acid can be selected from inorganic acids such as hydrochloric acid, sulfuric acid, nitric acid and phosphoric acid, and organic acids such as acetic acid.

In addition to the above acid aqueous solutions, the washing solution can be appropriately selected from aqueous solutions of various kinds of bases and salts.

The base can be selected from inorganic bases such as sodium hydroxide, potassium hydroxide and sodium carbonate, and organic bases such as triethylamine.

The salt can be selected from sodium chloride, sodium sulfate and the like.

The washing with water and the washing with solution may be performed in an order determined in consideration of the type of a substance to be removed, compatibility with the subsequent step, and the like. For instance, the washing with acid aqueous solution may be preceded by the washing with water.

The temperature of the water or the acid aqueous solution used for washing may be appropriately determined in consideration of the boiling point of water, the boiling point of an organic solvent constituting the organic layer, and the like.

Specifically, the temperature suitable for washing preferably falls within a range from 5 degrees C. to 95 degrees C., more preferably from 10 degrees C. to the boiling point of the organic solvent, the most preferably from 15 degrees C. to the boiling point of the organic solvent minus 5 degrees C.

By limiting the temperature to 95 degrees C. or less, the evaporation amount of the water layer and the organic layer can be reduced for stable washing. In addition, by limiting the temperature to 5 degrees or more, the impurities can be smoothly moved to the water layer during washing to improve removal efficiency.

For instance, when methylene chloride is used as the organic solvent under normal pressure, the temperature thereof preferably falls within a range from 5 degrees C. to 40 degrees C., more preferably from 10 degrees C. to 35 degrees C., particularly preferably from 15 degrees C. to 35 degrees C., the most preferably from 25 degrees C. to 35 degrees C.

For the washing, the volume ratio (water ratio) of the water layer to the total liquid layer (water layer+organic layer) preferably falls within a range from 5 vol % to 95 vol %, more preferably from 10 vol % to 70 vol %, particularly preferably from 20 vol % to 60 vol %, the most preferably from 30 vol % to 50 vol %. With the water layer ratio of 95 vol % or less, the ratio of the organic layer to a container subjected to the washing process can be increased in an economically favorable manner. In addition, with the water ratio of 5 vol % or more, a large amount of impurities can be removed by performing the washing process once, so that the impurities can be reduced to a predetermined level by repeating the washing with water only a few times.

The salt removable by the washing with water, acid aqueous solution or the like is exemplified by the salt of the aliphatic tertiary amine used for producing the bischloroformate compound of the formula (1), carbonate generated after decomposition of the phosgene, or the like.

The amount of a salt residue is preferably 1000 mass ppm or less relative to the produced bischloroformate compound of the formula (1), more preferably 700 mass ppm or less, particularly preferably 350 mass ppm or less, the most preferably 100 mass ppm or less.

By limiting the amount of the salt residue to 1000 mass ppm or less, it is possible to suppress the influence of the salt residue on the properties of the resulting bischloroformate compound of the formula (1).

In addition to the amine salt, a carbamate compound is also removable by the washing with water, acid aqueous solution or the like. Examples of the carbamate compound include diethylcarbamic acid, diethylcarbamic acid chloride and N,N,N',N'-tetraethylurea.

The amount of a carbamate compound residue is preferably 500 mass ppm or less relative to the bischloroformate compound, more preferably 150 mass ppm or less, particularly preferably 50 mass ppm or less, the most preferably 20 mass ppm or less.

With the amount of 500 mass ppm or less, when the bischloroformate compound of the formula (1) is required to exhibit electrical properties depending on the application thereof, the bischloroformate compound can exhibit favorable electrical properties.

Further, in addition to the amine salt, a phenol compound is also removable by the washing with water, acid aqueous solution or the like. An example of the phenol compound is a dihydric bisphenol compound usable as an ingredient. The amount of a phenol compound residue is preferably 5 mass % or less relative to the bischloroformate compound, more preferably 2 mass % or less, particularly preferably 0.5 mass % or less, the most preferably 0.1 mass % or less.

With the amount of 5 mass % or less, it is possible to reduce a compound with a hydroxyl terminal group in the bischloroformate compound, so that when the bischloroformate compound is required to exhibit electrical properties depending on the application thereof, the bischloroformate compound can exhibit favorable electrical properties.

As described above, preferably, the organic layer is washed to provide the bischloroformate compound of the formula (1). The organic solvent of the organic layer may be evaporated to be removed after purification, thereby providing the bischloroformate compound of the formula (1) in liquid or solid phase.

Such a bischloroformate compound of the formula (1) is usable as an ingredient for a polymer. The resulting polymer allows the bischloroformate compound of the formula (1) and other monomer to alternately exist therein, and thus the structure thereof can be more flexibly controlled using a copolymer provided by a typical synthesis method.

The biphenol compound of the formula (5) or the bisphenol compound of the formula (6) may be used as the dihydric phenol compound of the formula (2) (an ingredient). In addition to the compounds represented by the formulae (5) and (6), any dihydric phenol compound represented by the formula (2) can be used for synthesis of the bischloroformate compound represented by the formula (1).

In the dropping step, the reaction temperature preferably falls within a range from −10 to 40 degrees C., more preferably from 0 to 30 degrees C. A preferable reaction temperature range in the reaction step following the dropping step is the same as above.

When the reaction temperature falls below −10 degrees C., the solubility of the bischloroformate is lowered, so that using a large amount of hydrophobic solvent is likely to be required. When the reaction temperature exceeds 40 degrees C., the resulting bischloroformate is likely to have more than 1.99 repeating units.

The reaction time preferably falls within a range from 0.1 to 100 hours, more preferably from 0.1 to 20 hours, particularly preferably from 0.1 to 6 hours. The reaction time means a duration from the start of dropping to the start of washing.

In adding water to the reaction solution to separate the water layer and the organic layer from each other after synthesis of the bischloroformate compound of the formula (1), the hydrogen ion concentration (pH) of the water layer is required to be at least 7 or less, preferably 4 or less, more preferably in a range from 1 to 3. By limiting the hydrogen ion concentration to 4 or less, it is possible to suppress hydrolysis of the bischloroformate compound. The hydrogen ion concentration is adjustable using hydrochloric acid or the like. The bischloroformate compound of the formula (3) or (4) can also be washed under the same hydrogen ion concentration as above.

The average number of repeating units (n) of the bischloroformate compound produced as described above falls within a range from 1.0 to 1.99, preferably from 1.0 to 1.5.

According to the bischloroformate production method according to the first exemplary embodiment, it is possible to produce a monomer-like bischloroformate with 1.99 or less repeating units, so that a refining process such as recrystallization can be omitted. Water does not exist in the reaction system between the phosgene compound and the dihydric phenol compound of the formula (2), so that hydrolysis of the resulting acid chloride hardly occurs. Thus, reaction control, such as pH adjustment, for suppressing hydrolysis is not necessary. In the bischloroformate compound according to this exemplary embodiment, unlike the bischloroformate with an ester bond disclosed in Patent Literature 4, esterolysis or transesterification with an ingredient does not occur during chloroformatizing, purification, or the like. Using the aliphatic tertiary amine, unlike using an aromatic tertiary amine, prevents the reaction solution from being unintentionally colored, so that the resulting bischloroformate compound can have a favorable color. Thus, a special refining process such as recrystallization is not required, so that production efficiency can be improved without lowering yield. Since a more monomer-like bischloroformate compound can be provided in a simple method as described above, productivity is improved.

The dihydric phenol compound represented by the formula (2) is only slightly soluble in a hydrophobic organic solvent. However, it is possible to completely or almost completely dissolve the dihydric phenol compound in a hydrophobic organic solvent by mixing an aliphatic tertiary amine therewith. This helps the dihydric phenol compound represented by the formula (2) to react with phosgene, so that the bischloroformate compound can be easily produced.

Second Exemplary Embodiment

Next, description will be made below on a bischloroformate compound production method according to the second exemplary embodiment of the invention.

The production method according to the second exemplary embodiment can employ the same dihydric phenol compound represented by the formula (2), aliphatic tertiary amine and hydrophobic organic solvent as those employed by the production method according to the first exemplary embodiment.

Likewise, in the second exemplary embodiment, the biphenol compound of the formula (5) or the bisphenol compound of the formula (6) may be used as an ingredient to produce the bischloroformate compound represented by the formula (3) or (4). In addition to the compounds represented by the formulae (5) and (6), any dihydric phenol compound represented by the formula (2) can be used to produce the bischloroformate compound represented by the formula (1).

Figure 2:
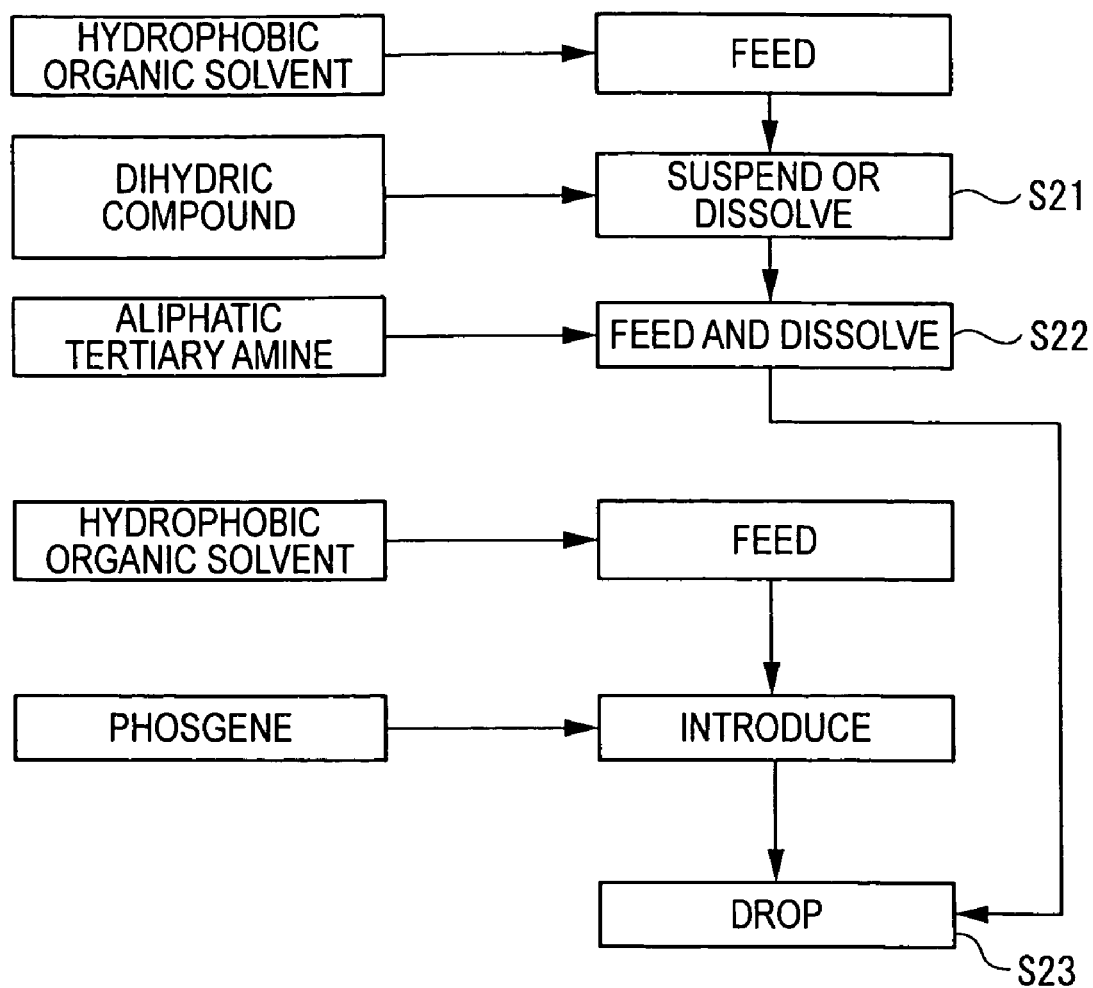
FIG. 2 is a flow chart showing a bischloroformate compound production method according to a second exemplary embodiment of the invention.

As shown in FIG. 2, the production method according to the second exemplary embodiment includes a suspending or dissolving step that suspends or dissolves the dihydric phenol compound represented by the formula (2) in a hydrophobic organic solvent (S21), an amine introducing step that introduces an aliphatic tertiary amine into the resulting suspension or solution (S22), and a dropping step that drops in phosgene the solution with the aliphatic tertiary amine introduced therein, the phosgene being diluted with a hydrophobic organic solvent (S23).

In the suspending or dissolving step, the dihydric phenol compound represented by the formula (2) is mixed with the hydrophobic organic solvent to prepare a suspension or solution. The prepared suspension or solution is mixed with the aliphatic tertiary amine to prepare a solution. The solution prepared in the amine introducing step is dropped in a phosgene solution for synthesis of the bischloroformate compound represented by the formula (1), the phosgene solution being prepared from phosgene and the hydrophobic organic solvent.

The bischloroformate production method according to the second exemplary embodiment provides the same advantages as those in the first exemplary embodiment.

Third Exemplary Embodiment

Next, description will be made below on a bischloroformate compound production method according to the third exemplary embodiment of the invention. In this exemplary embodiment, descriptions on the same arrangements as those in the above exemplary embodiments are omitted.

Figure 3:
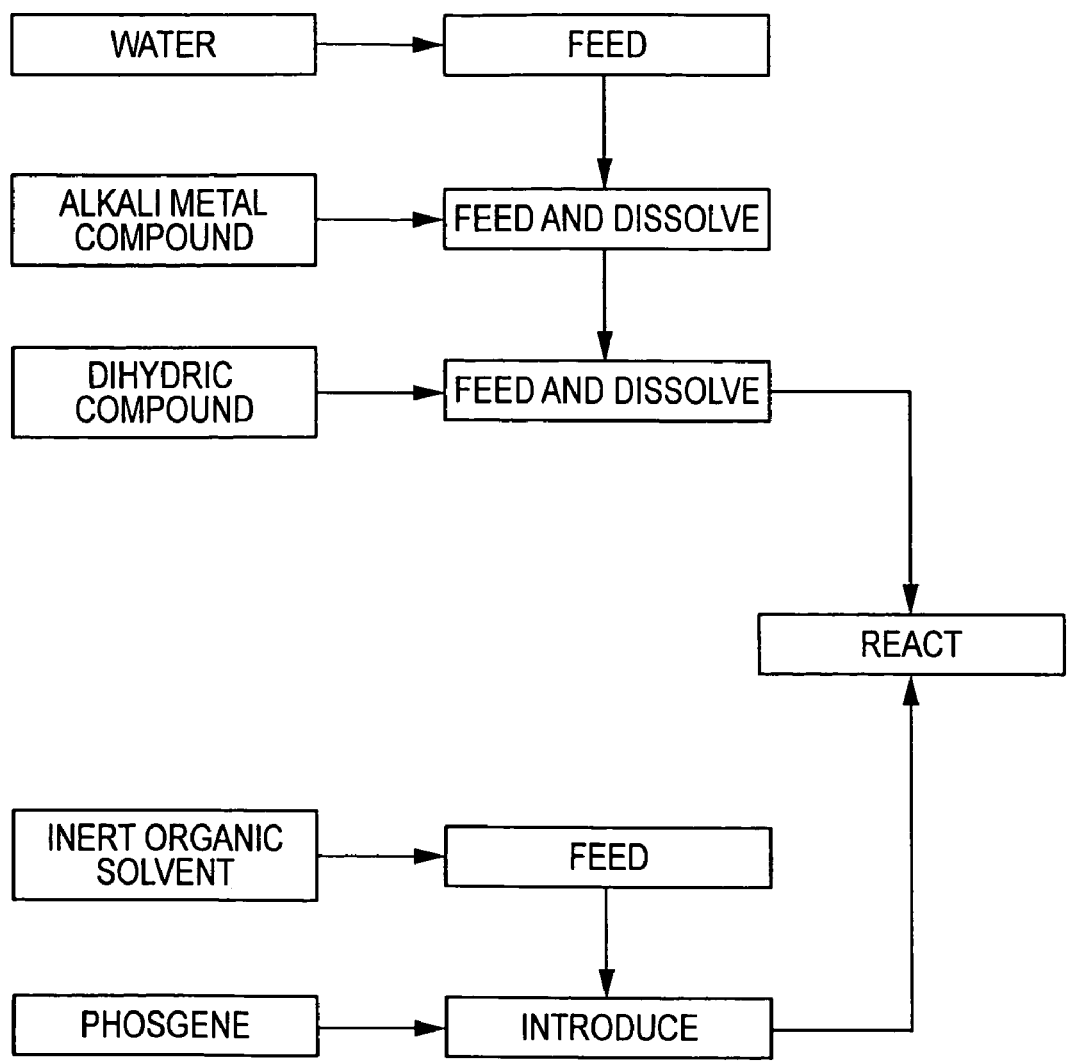
FIG. 3 is a flow chart showing a bischloroformate compound production method according to a third exemplary embodiment of the invention.

As shown in FIG. 3, a bischloroformate compound represented by the following formula (1) is provided by continuously reacting a material solution with a phosgene compound in a fine flow path in a micrometer order under the presence of an inert organic solvent, the material solution being provided by dissolving a dihydric phenol compound represented by the following formula (2) in an alkali aqueous solution.

Formula 19

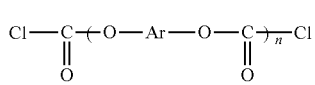

Formula (1)

Formula 20

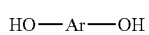

Formula (2)

In the formulae (1) and (2), Ar is a divalent aromatic group.

Preferably, the bischloroformate compound represented by the formula (1) is a bischloroformate compound represented by the following formula (3) or (4), and the dihydric phenol compound represented by the formula (2) is a biphenol compound represented by the following formula (5) or a bisphenol compound represented by the following formula (6).

The formulae (3) to (6) are the same as those in the first exemplary embodiment, and thus the descriptions thereof are omitted.

Formula 21

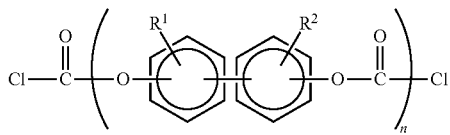

Formula (3)

Formula 22

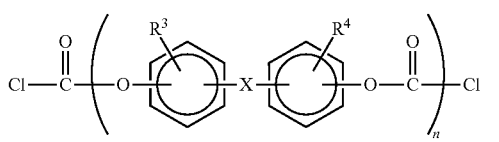

Formula (4)

Formula 23

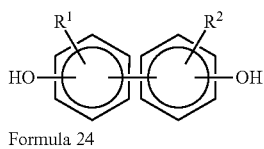

Formula (5)

Formula 24

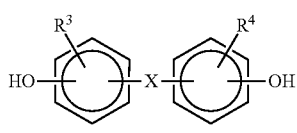

Formula (6)

The material solution is provided by, for instance, dissolving the dihydric phenol compound represented by the formula (2) in the alkali aqueous solution in which sodium hydroxide is dissolved in water.

In addition to the sodium hydroxide, usable are alkali metal hydroxides such as potassium hydroxide, lithium hydroxide and cesium hydroxide and alkali metal carbonates such as potassium carbonate.

The water may be any one of normal water such as tap water, distilled water, and ion-exchange water. Such normal water, distilled water and ion-exchange water may be deaerated under a reduced pressure, or be cooled under a stream of nitrogen gas after being boiled.

The phosgene solution is a solution in which a phosgene compound is dissolved in a predetermined inert organic solvent. The inert organic solvent is preferably a hydrophobic organic solvent, examples of which include aromatic hydrocarbons such as toluene, xylene and benzene, and aliphatic hydrocarbons such as pentane, heptane, hexane, octane, isooctane, cyclobutane, cyclopentane, cyclohexane and 1,3-dimethylcyclohexane, dichloromethane, and chloroform. One of the above may be singularly used or, alternatively, two or more may be used in combination. The inert organic solvent may also be a hydrophilic organic solvent such as tetrahydrofuran.

The inert organic solvent is not particularly limited in used amount, but is preferably used at an amount of 3 to 50 weight by part of the dihydric phenol compound represented by the formula (2), more preferably 5 to 20 weight by part.

Examples of the phosgene compound include monophosgene, diphosgene and triphosgene, one of which may be singularly used or, alternatively, two or more may be used in combination.

The used amount of the phosgene compound is not particularly limited, but is 0.95 equivalent weight or more relative to a hydroxyl group in the dihydric phenol compound of the formula (2), preferably 10 equivalent weight or more, more preferably in a range from 1.0 to 3.0 equivalent weight. By using the phosgene compound at an amount corresponding to an excessive amount of alkali or more, the reacted mixture can have a relatively high hydrogen ion concentration, so that it is possible to prevent the bischloroformate compound from reacting with the alkali water during liquid separation. Further, the bischloroformate compound can also be prevented from reacting with the alkali water by suppressing the used amount of the phosgene compound and adding an acid solution corresponding to an excessive amount of alkali at a mixer outlet.

Figure 4:
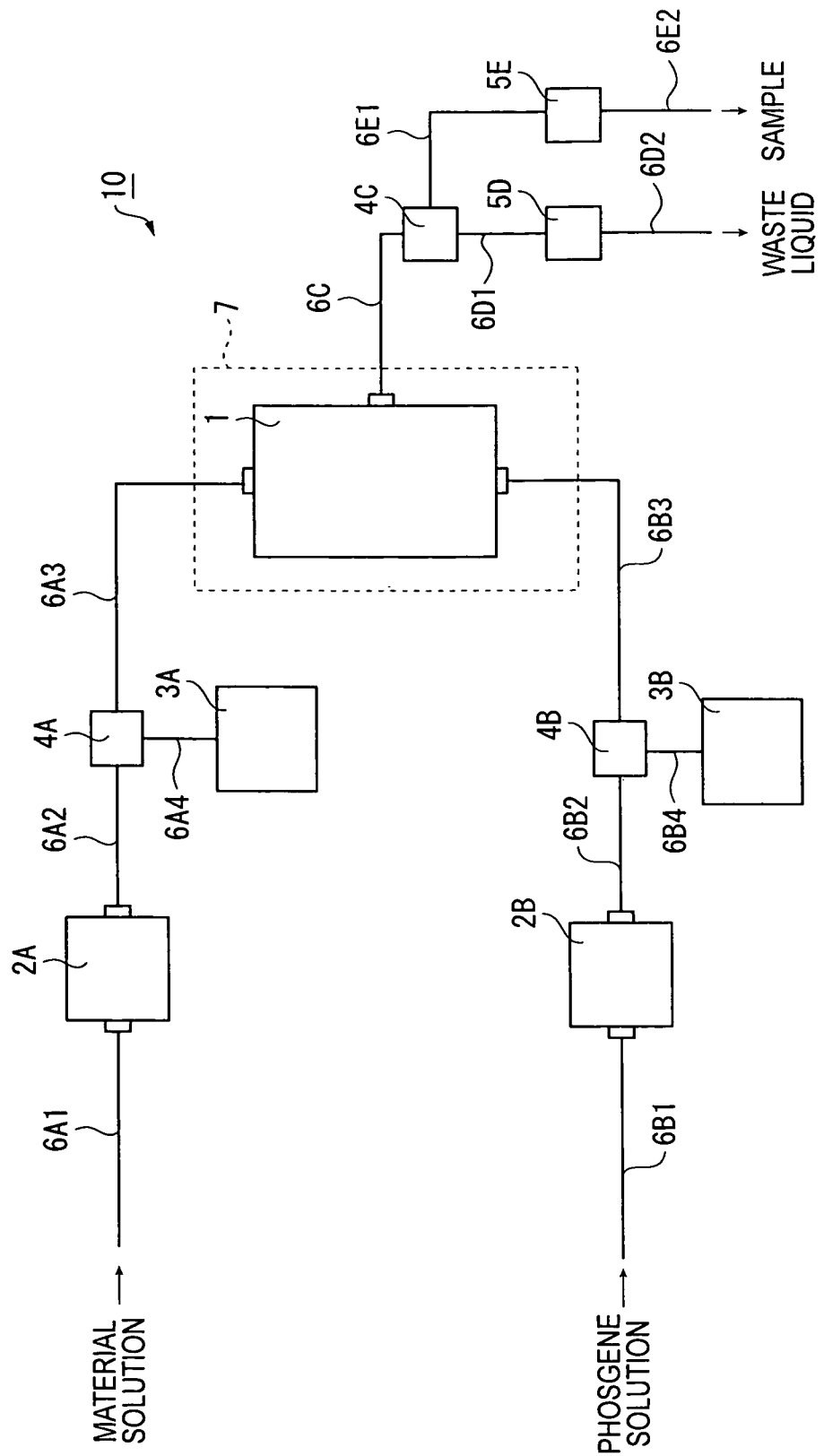
FIG. 4 is a schematic view showing a production device adapted to produce a bischloroformate compound according to the third exemplary embodiment.

As shown in FIG. 4, the bischloroformate compound represented by the formula (1) is produced using a production device 10. In this exemplary embodiment, the biphenol compound represented by the formula (5) or the bisphenol compound represented by the formula (6) may be used as the dihydric phenol compound represented by the formula (2) to produce the bischloroformate compound represented by the formula (3) or (4).

The production device 10 is adapted to continuously produce the bischloroformate compound represented by the formula (1), and includes supply pumps 2A and 2B, branch couplings 4A, 4B and 4C, pressure gauges 3A and 3B, a reactor 1, on-off valves 5D and 5E, and pipes 6A1, 6A2, 6A3, 6A4, 6B1, 6B2, 6B3, 6B4, 6C, 6D1, 6D2, 6E1 and 6E2.

The supply pump 2A is configured to continuously suck a material solution, having the dihydric phenol compound represented by the formula (2) dissolved in an alkali aqueous solution, from a material tank containing the material solution (not shown) through the pipe 6A1, to control the flow rate of the material solution to a predetermined level, and to introduce the material solution into the reactor 1 through the pipe 6A2, the branch coupling 4A and the pipe 6A3.

The pressure gauge 3A is connected to the branch coupling 4A via the pipe 6A4 to detect the pressure of the material solution flowing at the predetermined flow rate.

The supply pump 2B is also configured to continuously suck a phosgene solution from a phosgene tank (not shown) containing the phosgene solution through the pipe 6B1, and introduce the phosgene solution into the reactor 1 through the pipe 6B2, the branch coupling 4B and the pipe 6B3.

The pressure gauge 3B is connected to the branch coupling 4B via the pipe 6B4 to detect the pressure of the phosgene solution flowing at the predetermined flow rate in the same manner as the pressure gauge 3A.

The reactor 1 is configured to mix the material solution supplied from the material tank and the phosgene solution supplied from the phosgene tank together, and includes a micro flow path reactor and a temperature adjusting tank 7 configured to control the temperature of the micro flow path reactor to a predetermined level.

In the micro flow path reactor, the material solution and the phosgene solution are mixed together so that the dihydric phenol compound represented by the formula (2) is reacted with phosgene to generate the bischloroformate compound represented by the formula (1). When the solvent of the phosgene solution is a hydrophobic organic solvent, the phosgene solution is less mixable with the material solution. However, since a reaction space is provided by a path of a few hundred μm, the phosgene solution and the material solution can be favorably mixed together.

In the micro flow path reactor, the linear velocity of the mixture of the material solution and the phosgene solution preferably falls within a range from 0.2 m/sec to 50 m/sec, more preferably 0.2 m/sec to 30 m/sec. When the linear velocity is less than 0.2 m/sec, the average number of repeating units (n) of the resulting bischloroformate compound of the formula (1) is unlikely to be 1.99 or less. In order to achieve a linear velocity over 50 m/sec, the material solution and the phosgene solution need to be injected into the micro flow path reactor with a considerably large pressure, which may require a special device.

The temperature of the micro flow path reactor preferably falls within a range from −10 degrees C. to 60 degrees C. using the temperature adjusting tank 7, more preferably from 0 degrees C. to 40 degrees C.

When the temperature of the micro flow path reactor is higher than 60 degrees C., the average number of repeating units (n) of the resulting bischloroformate is unlikely to be 1.99 or less.

The reaction liquid of the bischloroformate compound provided through the micro flow path reactor flows into the branch coupling 4C through the pipe 6C.

The branch coupling 4C is connected to the on-off valve 5D through the pipe 6D1 and to the on-off valve 5E through the pipe 6E1. By opening the on-off valve 5D while closing the on-off valve 5E, an unnecessary liquid in the micro flow path reactor can be discharged as waste liquid. By closing the on-off valve 5D while opening the on-off valve 5E, the bischloroformate compound generated through the micro flow path reactor can be taken out.

Next, description will be made on a process of producing a bischloroformate compound using the production device 10.

The on-off valve 5D is opened and the on-off valve 5E is closed to wash the inside of components such as the micro flow path reactor using a predetermined washing liquid. After the washing, the on-off valve 5E is opened and the on-off valve 5D is closed.

The material solution is stored in the material tank, and the phosgene solution is stored in the phosgene tank. The supply pump 2A is driven and controlled such that the material solution is supplied to the reactor 1 at the predetermined flow rate. The supply pump 2B is driven and controlled such that the phosgene solution is supplied to the reactor 1 at a predetermined flow rate. With the above arrangement, the material solution reaches the reactor 1 through the pipe 6A1, the supply pump 2A, the pipe 6A2, the branch coupling 4A and the pipe 6A3. The phosgene solution reaches the reactor 1 through the pipe 6B1, the supply pump 2B, the pipe 6B2, the branch coupling 4B and the pipe 6B3.

The pressure of the material solution can be detected by the pressure gauge 3A. The pressure of the phosgene solution can be detected by the pressure gauge 3B.

The material solution and phosgene solution supplied to the reactor 1 flow into a flow path inside the micro flow path reactor. The temperature adjusting tank 7 has been driven so that the micro flow path reactor is set at a predetermined temperature during the inflow of these solutions. In the micro flow path reactor, the material solution and the phosgene solution are mixed together to generate the bischloroformate compound of the formula (1). After flowing out of the micro flow path reactor, the reaction solution of the bischloroformate of the formula (1) flows through the pipe 6C, the branch coupling 4C, the pipe 6E1, the on-off valve 5E and the pipe 6E2, and is subjected to sampling.

The bischloroformate compound produced using the production device 10 has an average number of repeating units (n) of 1.99 or less, the average number of repeating units (n) being calculated by the following equation (1).

$$\text{Average Number of Repeating Units }(n)=1+(M_{av}-M1)/M2 \quad \text{Equation (1)}$$

In the equation (1), Mav is (2×1000/(CF value)), M2 is (M1−98.92), M1 is a molecular weight of the bischloroformate compound when n=1 in the formula (1), the CF value (N/kg) is (CF number/concentration), the CF number (N) is a chlorine molecule number of the bischloroformate compound represented by the formula (1) contained in a 1L reaction solution, and the concentration (kg/L) is the amount of a solid resulting from condensation of the 1 L reaction solution. 98.92 is the total atomic weight of the two chlorine atoms, the one oxygen atom and the one carbon atom outside n repeating units in the formula (1).)

The average number of repeating units (n) preferably falls within a range from 1.0 to 1.99, more preferably from 1.0 to 1.5. When the average number of repeating units (n) is more than 1.99, a by-product is unlikely to be sufficiently removed by merely washing the bischloroformate-containing reaction solution with water. When the bischloroformate whose average number of repeating units (n) is more than 1.99 is used as an ingredient for a copolymer, for instance, it is likely to be difficult to increase the content ratio of comonomer, which results in a limited usage.

The third exemplary embodiment can provide the following advantages.

The material solution containing the dihydric phenol compound represented by the formula (2) and the phosgene solution containing the phosgene compound are continuously reacted with each other in the fine flow path in a micrometer order to produce the bischloroformate compound that is represented by the formula (1) and has an average number of repeating units (n) of 1.99 or less.

Since the space in which the solutions are mixed together is a fine flow path, the dihydric phenol compound represented by the formula (2) and phosgene are easily mixed together, thereby preventing oligomerization and polymerization of the dihydric phenol compound of the formula (2). Thus, it is possible to favorably obtain a monomer-like bischloroformate compound having an average number of repeating units (n) of 1.99 or less.

Since the resulting bischloroformate compound has an average number of repeating units (n) of 1.99 or less, the bischloroformate compound can be used as an ingredient for a PC copolymer without a refining process such as recrystallization. Thus, the PC copolymer can be produced in a facilitated manner.

Modifications

The bischloroformate compounds produced according to the first, second and third exemplary embodiments are exemplarily used as an ingredient for polycarbonate in the above descriptions, but are not limited thereto. Any one of the bischloroformate compounds produced according to the exemplary embodiments may be subjected to an oxidation process to become a peroxide to be usable as an oxidizer or a polymerization catalyst, and also usable as an intermediate for medicines or agricultural chemicals.

EXAMPLES

With reference to Examples and Comparatives, the invention will be described further in more detail. Incidentally, the descriptions on Examples are not intended to limit the invention in any way.

Description will first be made on Example 1-1 to Example 1-11 of the bischloroformate compound production method according to the first exemplary embodiment.

Example 1-1

A solution having 59.8 g (0.591 mol) triethylamine (hereinafter abbreviated as "TEA") diluted with 100 ml MDC was dropped in a mixture of 50.0 g (0.269 mol) 4,4'-biphenol, 500 ml dichloromethane (hereinafter abbreviated as "MDC") and 80.0 g (0.809 mol) phosgene at 13 to 16 degrees C. for 3 hours and 6 minutes. The reaction mixture was stirred at 14 to 16 degrees C. for 1 hour and 38 minutes. The reaction mixture was added with 5.0 ml concentrated hydrochloric acid and 200 ml pure water to be washed. Washing with water was repeated until the water layer became neutral. The extracted MDC solution was 897.5 g of a bischloroformate-compound-containing solution.

Example 1-2

A mixture of 29 g (0.287 mol) TEA and 70 ml MDC was dropped in a mixture of 35 g (0.13 mol) 1,1-bis-(4-hydroxyphenyl)cyclohexane (bisphenol Z, hereinafter abbreviated as "BPZ"), 525 ml MDC and 38.7 g (0.39 mol) phosgene at 5 to 17 degrees C. for 3 hours. After the dropping, the reaction mixture was stirred at 15 to 15.5 degrees C. for 1 hour, and then was added with 2.4 ml concentrated hydrochloric acid and 140 ml pure water to be washed. Washing with water was repeated until the water layer became neutral. An MDC layer was condensed under a reduced pressure. As a result, 319.9 g of a bischloroformate-compound-containing solution was obtained.

Example 1-3

In Example 1-3, description will be made on an example using triphosgene as a phosgene compound.

A solution having 38.7 g (0.13 mol) triphosgene(bis(trichloromethyl)carbonate dissolved in 200 ml MDC was dropped in a mixture of 35 g (0.13 mol) BPZ and 325 ml MDC at 3 to 5 degrees C. for 26 minutes. A mixture of 29 g (0.287 mol) TEA and 70 ml MDC was further dropped in the mixture of BPZ and MDC at 11 to 18 degrees C. for 3 hours. After the dropping, the reaction mixture was stirred at 17 to 17.5 degrees C. for 1 hour, and then was added with 2.4 ml concentrated hydrochloric acid and 140 ml pure water to be washed. Washing with water was repeated until the water layer became neutral. As a result of condensation of the extracted MDC layer under a reduced pressure, 319.7 g of a bischloroformate-compound-containing solution was obtained.

Example 1-4

A mixture of 223.9 g (2.21 mol) TEA and 460 ml MDC was dropped in a mixture of 230 g (1.01 mol) bis(3-methyl-4-hydroxyphenyl)methane (hereinafter abbreviated as "Bis-OCF"), 1058 ml MDC and 223 g (2.25 mol) phosgene at 15.5 to 19 degrees C. for 3 hours and 3 minutes. After the dropping, the reaction mixture was stirred at 16 to 18 degrees C. for 1 hour, and then was added with 21 ml concentrated hydrochloric acid and 920 ml pure water to be washed. Washing with water was repeated until the water layer became neutral. Thus, an MDC layer was extracted. As a result, 1760.8 g of a bischloroformate-compound-containing solution was obtained.

Example 1-5

In Example 1-5, description will be made on an example using triphosgene as a phosgene compound.

A mixture of 17.0 g (0.168 mol) TEA and 35 ml MDC was dropped in a mixture of 17.5 g (0.077 mol) Bis-OCF, 83 ml MDC and 16.7 g (0.056 mol) triphosgene at 9 to 19 degrees C. for 1 hour and 53 minutes. After the dropping, the reaction mixture was stirred at 15.5 to 17.5 degrees C. for 1 hour, and then was added with 1.2 ml concentrated hydrochloric acid and 70 ml pure water to be washed. Washing with water was repeated until the water layer became neutral. By extracting an MDC layer, 129.1 g of a bischloroformate-compound-containing solution was obtained.

Example 1-6

A mixture of 23.2 g (0.229 mol) TEA and 66 ml MDC was dropped in a mixture of 33.0 g (0.103 mol) 2,2-bis(4-hydroxyphenyl)adamantane, 330 ml MDC and 30.6 g (0.309 mol) phosgene. The other operations were the same as those in Example 1-1. As a result, 288.2 g of a bischloroformate-containing solution was obtained.

Example 1-7

A mixture of 28.8 g (0.285 mol) TEA and 80 ml MDC was dropped in a mixture of 33.0 g (0.129 mol) bis(2,5-dimethyl-4-hydroxyphenyl)methane, 330 ml MDC and 38.2 g (0.386 mol) phosgene. The other operations were the same as those in Example 1-1. As a result, 268.6 g of a bischloroformate-containing solution was obtained.

Example 1-8

A mixture of 6.3 g (0.062 mol) TEA and 20 ml MDC was dropped in a mixture of 10.0 g (0.028 mol) 1,1-bis(4-hydroxyphenyl)cyclododecane, 100 ml MDC and 8.4 g (0.085 mol) phosgene. The other operations were the same as those in Example 1-1. As a result, 76.4 g of a bischloroformate-containing solution was obtained.

Example 1-9

A mixture of 199.4 g (1.97 mol) TEA and 460 ml MDC was dropped in a mixture of 230 g (0.897 mol) 2,2-bis(3-methyl-4-hydroxyphenyl)propane, 1058 ml MDC and 187 g (1.89 mol) phosgene. The other operations were the same as those in Example 1-1. As a result, 1848.4 g of a bischloroformate-containing solution was obtained.

Example 1-10

A mixture of 146.8 g (1.45 mol) TEA and 500 ml MDC was dropped in a mixture of 250 g (0.661 mol) 9,9-bis(3-methyl-4-hydroxyphenyl)fluorene (hereinafter abbreviated as "BCF"), 1175 ml MDC and 148 g (1.50 mol) phosgene. The other operations were the same as those in Example 1-1. As a result, 2944.5 g of a bischloroformate-containing solution was obtained.

Example 1-11

60.0 kg (224 mol) BPZ was suspended with 1080 L methylene chloride, and then was dissolved by adding 66.0 kg (667 mol) phosgene thereto. Further, a solution having 44.0 kg (435 mol) triethylamine dissolved in 120 L methylene chloride was dropped in the above reactant at 2.2 to 17.8 degrees C. for 2 hours and 50 minutes. After being stirred at 17.9 to 19.6 degrees C. for 30 minutes, 900 L methylene chloride was evaporated to be removed at 14 to 20 degrees C. The liquid residue was added with 210 L pure water, 1.2 kg concentrated hydrochloric acid and 450 g hydrosulfite, and was washed at 30 degrees C. for 15 minutes. Subsequently, washing with 210 L pure water was repeated for three times. As a result, a bischloroformate-containing solution (BPZ oligomer methylene chloride solution) was obtained.

The content of the carbamate compound contained in the bischloroformate-containing solution obtained in Example 1-11 was measured. Specifically, the resulting bischloroformate-containing solution was dried under a reduced pressure to become a solid, and then a nitrogen amount was calculated by total nitrogen analyzer on a chemiluminescence method. From the resulting value, a nitrogen amount derived from triethylamine, which was separately quantified by GC (Gas Chromatography), was deducted. The rest of the nitrogen amount was calculated as a nitrogen amount derived from the carbamate compound.

As a result, the nitrogen concentration derived from the carbamate compound contained in the solid of the resulting bischloroformate was 80 mass ppm. Incidentally, the nitrogen amount derived from the triethylamine was 0.3 mass ppm.

The total nitrogen amount was quantified in accordance with JIS K2609 (chemiluminescence method) using TS-100 manufactured by Mitsubishi Chemical Analytech Co., Ltd. The JIS standard provides a measurement method for liquid, but the same device was used for measurement of a solid sample.

Methylene chloride was removed from the methylene chloride solution of the bischloroformate compound at 50 degrees C. under a reduced pressure, and the bischloroformate compound was dried to be solidified. The resulting solid was measured. The result of this measurement was compared with an analytical curve separately made using pyridine as a standard substance, thereby quantifying the nitrogen amount. The obtained result was converted at the concentration of the bischloroformate compound in the methylene chloride to calculate the total nitrogen amount in the bischloroformate compound.

For quantifying triethylamine, 0.5N—NaOH aqueous solution was added to the solid of the bischloroformate compound obtained in the above method so that the pH thereof becomes 8 or more, and chloroform was further added thereto. The chloroform extract (i.e., triethylamine) was subjected to a gas chromatography analysis to be quantified in an absolute calibration method.

Conditions for the gas chromatography analysis were as follows.
Model: 7890A manufactured by Agilent Technologies, Inc.
Column: CP-VOLAMINE (manufactured by Varian, Inc.) 60 m×0.32 mm (inner diameter)
Inlet Temperature: 150 degrees C.
Column Temperature The column temperature was raised from 40 degrees C. to 150 degrees C. by 50 degrees C. per minute, maintained at 150 degrees C. for 10 minutes, and raised to 250 degrees C. by 50 degrees C. per minute.
Carrier Gas: Helium 40 cm per second (constant)
Injected Amount: 2 µl
Injection Method: Splitless
Detector: FID
FID Temperature: 260 degrees C.

Next, description will be made on Example 2-1 to Example 2-5 of the bischloroformate compound production method according to the second exemplary embodiment.

Example 2-1

73.0 g (0.272 mol) BPZ and 410 ml MDC were mixed to provide a suspended solution. The suspended solution was added with 55.3 g (0.546 mol) TEA to be dissolved. The above reaction mixture was dropped in a solution having 54.5 g (0.551 mol) phosgene dissolved in 225 ml MDC at 14 to 18.5 degrees C. for 2 hours and 50 minutes. After the dropping, the reaction mixture was stirred at 18.5 to 19 degrees C. for 1 hour, and then 250 ml MDC was evaporated to be removed therefrom at 10 to 22 degrees C. The liquid residue was added with 4.5 ml concentrated hydrochloric acid and 73 ml pure water to be washed, and then washing with water was repeated until the water layer became neutral.

The resulting MDC solution was 574.6 g of a bischloroformate-compound-containing solution.

Example 2-2

A solution prepared from 73.0 g (0.341 mol) 1,1-bis(4-hydroxyphenyl)ethane, 410 ml MDC and 68.7 g (0.679 mol) TEA was dropped in a solution having 65.0 g (0.657 mol) phosgene dissolved in 245 ml MDC. The other operations were the same as those in Example 2-1. As a result, 622.2 g of a bisphenol-compound-containing solution was obtained. Incidentally, the MDC amount was adjusted so that the concentration of the reaction solution fell within a range from 0.20 to 0.30 kg/L.

Example 2-3

A solution prepared from 47.0 g (0.124 mol) BCF, 265 ml MDC and 25.7 g (0.254 mol) TEA was dropped in a solution having 24.8 g (0.251 mol) phosgene dissolved in 147 ml MDC. The other operations were the same as those in Example 2-1. As a result, 293.5 g of a bisphenol-compound-containing solution was obtained. Incidentally, the MDC amount was adjusted so that the concentration of the reaction solution fell within a range from 0.20 to 0.30 kg/L.

Example 2-4

A solution prepared from 80.2 g (0.351 mol) 2,2-bis(4-hydroxyphenyl)propane, 450 ml MDC and 70.4 g (0.696 mol) TEA was dropped in a solution having 69.8 g (0.706 mol) phosgene dissolved in 250 ml MDC. The other operations were the same as those in Example 2-1. As a result, 695.1 g of a bisphenol-compound-containing solution was obtained. Incidentally, the MDC amount was adjusted so that the concentration of the reaction solution fell within a range from 0.20 to 0.30 kg/L.

Example 2-5

A solution having a mixture of 85.7 g (0.32 mol) BPZ, 111 ml MDC and 64.2 g (0.634 mol) TEA dissolved was dropped in a solution having 62.1 g (0.209 mol) triphosgene dissolved in 85 ml MDC at 6 to 15 degrees C. for 3 hours and 5 minutes. After the dropping, the reaction mixture was stirred at 15 to 20 degrees C. for 1 and 50 minutes, and was dropped. After the dropping, the reaction mixture was stirred at 8 to 19 degrees C. for 2 hours, and then was added with 5.2 ml concentrated hydrochloric acid and 82 ml pure water to be washed. Washing with water was repeated until the water layer became neutral. As a result, 720.8 g of a bischloroformate-compound-containing solution was obtained.

Next, description will be made on Experimental Examples 3-1 to 3-4 for evaluating a polycarbonate oligomer produced using a bischloroformate compound as an ingredient and Comparative Experimental Example 1.

Experimental Example 3-1

600 g (2.24 mol) BPZ and 2040 ml MDC were mixed to provide a suspended solution. The suspended solution was added with 461.4 g (4.56 mol) TEA to be dissolved. The above mixture was dropped in a solution having 437.9 g (4.43 mol) phosgene dissolved in 1200 ml MDC at 5 to 11 degrees C. for 2 hours and 46 minutes. The other operations were the same as those in Example 2-1. As a result, 4311.6 g of a bischloroformate-compound-containing solution was obtained. Incidentally, the MDC amount was adjusted so that the concentration of the reaction solution fell within a range from 0.20 to 0.30 kg/L.

The solvent was removed from the resulting bischloroformate reaction solution, and then 5.4 g of the bischloroformate reaction solution was dissolved in 60 mL methylene chloride. The above mixture was added with a solution having 3.5 g 1,1-bis(4-hydroxyphenyl)cyclohexane dissolved in 22 mL potassium hydroxide (2N), added with 30 mg p-tert-butylphenol (PTBP) and stirred, and added with 0.2 mL triethylamine aqueous solution (7%) and intensely stirred. After being stirred for 1 hour, the mixture was subjected to washing with 200 mL water, washing with 0.1N hydrochloric acid (100 mL), and washing with 100 mL water (twice) in this sequence. The resulting polycarbonate oligomer solution was poured into methanol, and was dried to become a solid. This solid exhibited a reduced viscosity $[\eta_{sp/c}]$ of 0.94 in 0.5 g/dl of the methylene chloride solution at 20 degrees C. The mole number ratio of the carbamate terminal group in all terminal groups of the resulting compound was calculated by comparing the integrated value of the peaks of all terminal groups and the integrated value of the peaks of the carbamate terminal group, the peaks being derived from the terminal components (OH terminal group, carbamate terminal group, chloroformate terminal group) measured by 1H-NMR.

Experimental Example 3-2

A mixture of 29.6 g (0.293 mol) TEA and 80 ml MDC was dropped in a mixture of 40 g (0.149 mol) BPZ, 600 ml MDC and 44.1 g phosgene at 25 to 32 degrees C. for 2 hours and 55 minutes. The other operations were the same as those in Example 1-2. As a result, 307.5 g of a bisphenol-compound-containing solution was obtained.

The resulting bischloroformate-compound-containing solution was processed in the same manner as in Experimental Example 3-1 to measure the reduced viscosity of the solid. The mole number ratio of the carbamate terminal group in all terminal groups of the resulting compound was also measured in the same manner as in Experimental Example 3-1.

Experimental Example 3-3

A mixture of 29.5 g (0.292 mol) TEA and 80 ml MDC was dropped in a mixture of 40 g (0.149 mol) BPZ, 600 ml MDC and 44.1 g phosgene at 4 to 8 degrees C. for 2 hours and 59 minutes. The other operations were the same as those in Example 1-2. As a result, 335.0 g of a bisphenol-compound-containing solution was obtained.

The resulting bischloroformate-compound-containing solution was processed in the same manner as in Experimental Example 3-1 to measure the reduced viscosity of the solid. The mole number ratio of the carbamate terminal group in all terminal groups of the resulting compound was also measured in the same manner as in Experimental Example 3-1.

Experimental Example 3-4

90 g (0.335 mol) BPZ and 306 ml MDC were mixed to provide a suspended solution. The suspended solution was added with 66.5 g (0.657 mol) TEA to be dissolved. The above mixture was dropped in a solution having 92.9 g (0.939 mol) phosgene dissolved in 180 ml MDC at 3 to 7 degrees C. for 3 hours and 5 minutes. The other operations were the same as those in Example 2-1. As a result, 675.5 g of a bisphenol-compound-containing solution was obtained. Incidentally, the MDC amount was adjusted so that the concentration of the reaction solution fell within a range from 0.20 to 0.30 kg/L.

The resulting bischloroformate-compound-containing solution was processed in the same manner as in Experimental Example 3-1 to measure the reduced viscosity $[\eta_{sp/c}]$ of the solid. The mole number ratio of the carbamate terminal group in all terminal groups of the resulting compound was also measured in the same manner as in Experimental Example 3-1.

Comparative Experimental Example 1

A mixture of 217 g (2.144 mol) TEA and 500 ml MDC was dropped in a mixture of 250 g (0.932 mol) BPZ, 4500 ml MDC and 276.5 g phosgene at 11 to 16 degrees C. for 2 hours and 57 minutes. The other operations were the same as those in Example 1-2. As a result, 2378.5 g of a bisphenol-compound-containing solution was obtained.

The resulting bischloroformate-compound-containing solution was processed in the same manner as in Experimental Example 3-1 to measure the reduced viscosity $[\eta_{sp/c}]$ of the solid. The mole number ratio of the carbamate terminal group in all terminal groups of the resulting compound was also measured in the same manner as in Experimental Example 3-1.

Impurities contained in the resulting bischloroformate compound weighted 3600 mass ppm in terms of nitrogen.

Tables 1 and 2 show the evaluation results of the bischloroformate compounds, bischloroformate-compound-containing solutions and polycarbonate oligomers obtained in Example 1-1 to Example 1-11, Example 2-1 to Example 2-5, Experimental Example 3-1 to 3-4, and Comparative Experimental Example 1. Incidentally, in Tables 1 and 2, the values of Concentration (kg/L), CF Number (N) and CF Value of Example 1-1 relate to a bischloroformate compound in a methylene chloride layer.

In Tables 1 and 2, the CF number was calculated by quantifying chlorine ions liberated by hydrolysis. Additionally, in Tables 1 and 2, the concentration was calculated by measuring the amount of a solid residue after removal of the solvent from the solution.

TABLE 1

|  | Concentration (kg/L) | CF Number (N) | CF Value | Average Number of Repeating Units (n) |
|---|---|---|---|---|
| Example 1-1 | 0.12 | 0.77 | 6.42 | 1.00 |
| Example 1-2 | 0.21 | 1.07 | 5.10 | 1.00 |
| Example 1-3 | 0.21 | 1.04 | 4.95 | 1.04 |
| Example 1-4 | 0.26 | 1.32 | 5.08 | 1.15 |
| Example 1-5 | 0.25 | 1.33 | 5.32 | 1.06 |
| Example 1-6 | 0.21 | 0.87 | 4.14 | 1.11 |
| Example 1-7 | 0.24 | 1.19 | 4.96 | 1.08 |
| Example 1-8 | 0.23 | 0.92 | 4.00 | 1.06 |
| Example 1-9 | 0.24 | 1.16 | 4.83 | 1.14 |
| Example 1-10 | 0.15 | 0.55 | 3.67 | 1.11 |
| Example 1-11 | 0.23 | 1.14 | 4.96 | 1.02 |
| Example 2-1 | 0.22 | 0.91 | 4.14 | 1.31 |
| Example 2-2 | 0.21 | 0.98 | 4.67 | 1.37 |
| Example 2-3 | 0.27 | 0.97 | 3.59 | 1.13 |
| Example 2-4 | 0.21 | 0.88 | 4.19 | 1.49 |
| Example 2-5 | 0.20 | 0.78 | 3.90 | 1.41 |

TABLE 2

|  | Concentration (kg/L) | CF Number (N) | CF Value | Average Number of Repeating Units (n) | Mole Ratio of Carbamate Terminal Group* (%) | Reduced Viscosity [$\eta_{sp/c}$] |
|---|---|---|---|---|---|---|
| Experimental Example 3-1 | 0.24 | 0.91 | 3.79 | 1.46 | 1.20 | 0.94 |
| Experimental Example 3-2 | 0.25 | 1.18 | 4.72 | 1.10 | 0.49 | 1.26 |
| Experimental Example 3-3 | 0.22 | 1.08 | 4.91 | 1.05 | 0.34 | 1.30 |
| Experimental Example 3-4 | 0.24 | 0.96 | 4.00 | 1.36 | 0.18 | 1.37 |
| Comparative Experimental Example 1 | 0.20 | 0.94 | 4.70 | 1.11 | 10.8 | 0.15 |

*"Mole Ratio of Carbamate Terminal Group (%)" means "a ratio of an amount by mole of the carbamate terminal group in all terminal groups of the resulting compound (%)".

Each of Example 1-1 to Example 1-11 and Example 2-1 to Example 2-5 provided a bischloroformate compound having an average number of repeating units of 1.99 or less. In each of Experimental Examples 3-1 to 3-4, the used amount of the aliphatic tertiary amine for the bischloroformatizing reaction was set at 1.1 equivalent weight or less, so that the mole ratio of the carbamate terminal group was favorably reduced to 10% or less, and thus the resulting polycarbonate oligomer had an increased molecule weight. In contrast, in Comparative Experimental Example 1, the used amount of the tertiary amine was 1.15 equivalent weight, so that the mole ratio of the carbamate terminal group exceeded 10%, and thus the resulting polycarbonate oligomer had a small molecule weight.

Next, description will be made on the bischloroformate compound production method according to the third exemplary embodiment with reference to Example 4-1 to Example 4-5 and Example 5-1 to Example 5-5. Incidentally, Example 4-1 to Example 4-5 employed a micromixer (YM-3 manufactured by Yamatake Corporation) as the micro flow path reactor of the above production device, and Example 5-1 to Example 5-5 employed a microreactor (micro process server MPS-α 100 manufactured by Hitachi Plant Technologies, Ltd.) as the micro flow path reactor.

Example 4-1

A material solution was prepared by mixing 11.9 g (0.298 mol) sodium hydroxide, 16.7 g (0.298 mol) potassium hydroxide, 317 ml water and d 40.0 g (0.149 mol) 1,1-bis-(4-hydroxyphenyl)cyclohexane (bisphenol Z, hereinafter abbreviated as "BPZ").

A phosgene solution was prepared by mixing 213 ml dichloromethane (hereinafter abbreviated as "MDC") and 38.8 g (0.392 mol) phosgene.

The micromixer was immersed in an ice bath in use.

For producing a bischloroformate compound, the flow rate of the material solution was set at 50 ml per minute, the flow rate of the phosgene solution was set at 37.2 ml per minute, and the linear velocity of a mixture of the material solution and the phosgene solution was set at 5.8 ml per second.

By limiting the flow rate of the material solution and the flow rate of the phosgene as above, it is theoretically expected to provide phosgene of 1.5 equivalent weight relative to the phenolic hydroxyl group of the BPZ.

The resulting bischloroformate compound was received in a receiver with a dilute hydrochloric acid aqueous solution therein. The bischloroformate compound solution collected in the receiver was washed to extract an MDC layer containing the bischloroformate compound therefrom.

Example 4-2

A bischloroformate compound was produced in the same manner as in Example 4-1 except that the flow rate of the material solution was set at 250 ml per minute, and the flow rate of the phosgene solution was set at 186 ml per minute for producing the bischloroformate compound.

Example 4-3

A material solution was prepared by mixing 12.0 g (0.300 mol) sodium hydroxide, 16.8 g (0.300 mol) potassium hydroxide, 330 ml water and 27.9 g (0.150 mol) biphenol. Incidentally, the water used in this example had been cooled under a stream of nitrogen after being boiled.

A phosgene solution was prepared by mixing 270 ml MDC and 38.2 g (0.386 mol) phosgene.

For producing a bischloroformate compound, the flow rate of the material solution was set at 200 ml per minute, and the flow rate of the phosgene solution was set at 200 ml per minute.

The conditions other than the above were the same as those in Example 4-1 for producing the bischloroformate compound.

Example 4-4

In this example, a material solution was prepared by mixing 52.8 g (1.32 mol) sodium hydroxide, 74.1 g (1.32 mol) potassium hydroxide, 1980 ml water and 250 g (0.66 mol) 4,4'-(fluorene-9-9-diyl)di-2-methylphenol.

A phosgene solution was prepared by mixing 1333 ml MDC and 194.1 g (1.96 mol) phosgene.

For synthesis of a bischloroformate compound, the material solution was fed at 250 ml per minute while the phosgene solution was fed at 162 ml per minute. The resulting bischloroformate compound solution was received in a receiver with a dilute hydrochloric acid therein. The bischloroformate compound solution collected in the receiver was washed to extract the MDC layer containing the bischloroformate compound therefrom.

The conditions other than the above were the same as those in Example 4-1 for producing the bischloroformate compound.

Example 4-5

A material solution was prepared from 44.8 g (0.12 mol) sodium hydroxide, 950 ml water and 120 g (0.56 mol) 1,1-bis(4-hydroxyphenyl)ethane (commonly called as bisphenol E).

A phosgene solution was prepared from 640 ml MDC and 177.1 g (1.79 mol) phosgene.

The flow rate of the material solution was set at 250 ml per minute, and the flow rate of the phosgene solution was set at 165 ml per minute.

The conditions other than the above were the same as those in Example 4-1. An MDC layer containing a bischloroformate compound was extracted.

Example 5-1

A solution was prepared by dissolving 16.4 g (0.41 mol) sodium hydroxide and 23.0 g (0.41 mol) potassium hydroxide in 436 ml water. 55.0 g (0.205 mol) BPZ was dissolved in the above solution to prepare a material solution.

A phosgene solution was prepared by dissolving 77.1 g (0.779 mol) phosgene in 293 ml MDC.

The resulting material solution and phosgene solution were mixed together in the microreactor to produce a bischloroformate compound. The flow rate of the material solution was 1.5 ml per minute, and the flow rate of the phosgene solution was 1.08 ml per minute.

The temperature of the microreactor was set at 0 degrees C.

Example 5-2

A bischloroformate compound was produced in the same manner as in Example 5-1 except that the reaction temperature was set at 20 degrees C.

Example 5-3

A bischloroformate compound was produced in the same manner as in Example 5-1 except that the reaction temperature was set at 40 degrees C.

Example 5-4

A bischloroformate compound was produced in the same manner as in Example 5-1 except that the reaction temperature was set at 60 degrees C.

Example 5-5

A material solution was prepared by dissolving 10.5 g (0.26 mol) sodium hydroxide in 238 ml water and further dissolving 30.0 (0.131 mol) bisphenol A therein.

A phosgene solution was prepared by dissolving 26.0 g (0.263 mol) phosgene in 160 ml MDC.

Using the microreactor in the same manner as in Example 5-1, the flow rate of the material solution and the flow rate of the phosgene solution were set as shown in Table 2, so that the material solution and the phosgene solution were fed in such a manner that a theoretical phosgene magnification became 1.5 equivalent weight.

The temperature of the microreactor was set at 60 degrees C.

Tables 3 and 4 show the evaluation results of the resulting bischloroformate compounds according to Example 4-1 to Example 4-5 and Example 5-1 to Example 5-5.

In Tables 3 and 4, the CF number was calculated by quantifying chlorine ions liberated by hydrolysis. Additionally, in Tables 3 and 4, the concentration was calculated by measuring the amount of a solid residue after removal of the solvent from the solution.

TABLE 3

|  | Example 4-1 | Example 4-2 | Example 4-3 | Example 4-4 | Example 4-5 |
| --- | --- | --- | --- | --- | --- |
| Reaction Temperature | Ice Bath | Ice Bath | Ice Bath | Ice Bath | Ice Bath |
| Flow Rate of Material Solution (ml/min) | 50 | 250 | 200 | 250 | 250 |
| Flow Rate of Phosgene Solution (ml/min) | 37.2 | 186 | 200 | 162 | 165 |
| Equivalent Weight Ratio of Phosgene Compound | 1.5 | 1.5 | 1.5 | 1.5 | 1.5 |
| Linear Velocity of Mixture (ml/sec) | 5.8 | 29 | 27 | 27 | 28 |
| pH of Water Layer in Receiver (Test Paper) | 9 | 1 | 1 | 1 | 1 |
| GPC Monomer (area %) | 64.4 | 86.1 | 91.4 | 96.5 | 96.2 |
| CF Number (N) | 0.88 | 1.21 | 0.86 | 0.87 | 1.76 |
| Concentration (Kg/L) | 0.215 | 0.251 | 0.14 | 0.23 | 0.32 |
| CF Value (N/Kg) | 4.1 | 4.82 | 6.14 | 3.78 | 5.52 |
| Average Number of Repeating Units (n) | 1.32 | 1.07 | 1.07 | 1.06 | 1.1 |

TABLE 4

|  | Example 5-1 | Example 5-2 | Example 5-3 | Example 5-4 | Example 5-5 |
| --- | --- | --- | --- | --- | --- |
| Reaction Temperature | 0 | 20 | 40 | 60 | 60 |
| Flow Rate of Material Solution (ml/min) | 1.5 | 1.5 | 1.5 | 1.5 | 1.5 |
| Flow Rate of Phosgene Solution (ml/min) | 1.08 | 1.08 | 1.08 | 1.08 | 1.45 |
| Linear Velocity of Mixture (ml/sec) | 0.22 | 0.22 | 0.22 | 0.22 | 0.25 |

TABLE 4-continued

|  | Example 5-1 | Example 5-2 | Example 5-3 | Example 5-4 | Example 5-5 |
|---|---|---|---|---|---|
| Equivalent Weight Ratio of Phosgene Compound | 2 | 2 | 2 | 2 | 1.5 |
| pH of Water Layer in Receiver (Test Paper) | 4 | 1 | 2 | 1 | 1 |
| GPC Monomer (area %) | 66.8 | 59.5 | 56.9 | 46.8 | 74 |
| CF Number (N) | 1.06 | 0.98 | 0.98 | 0.77 |  |
| Concentration (Kg/L) | 0.262 | 0.257 | 0.256 | 0.232 |  |
| CF Value (N/Kg) | 4.06 | 3.83 | 3.82 | 3.34 |  |
| Average Number of Repeating Units (n) | 1.34 | 1.44 | 1.44 | 1.7 | 1.2 |

It has been demonstrated that all of Example 4-1 to Example 4-5 and Example 5-1 to Example 5-5, except for Example 5-4, provide bischloroformate compounds each having an average number of repeating units (n) of 1.5 or less. In particular, it has been demonstrated that Example 4-2 to Example 4-5 using the micromixer provide bischloroformate compounds each having an average number of repeating units of 1.1 or less.

The invention claimed is:

1. A bischloroformate compound production method of producing a bischloroformate compound represented by a formula (1) below, the method comprising:

mixing a dihydric phenol compound represented by a formula (2) below, a phosgene compound, and an aliphatic tertiary amine together using a hydrophobic organic solvent to produce bischloroformate represented by the formula (1), the bischloroformate having an average number of repeating units (n) of 1.99 or less, the average number of repeating units (n) being calculated by an equation (1) below:

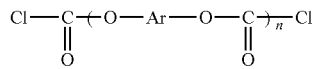

Formula (1)

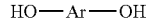

Formula (2)

where Ar of the formulae (1) and (2) is a divalent aromatic group; and

Average Number of Repeating Units $(n) = 1 + (Mav - M1)/M2$  (Equation 1)

where Mav is $(2 \times 1000/(CF \text{ value}))$, M2 is (M1−98.92), M1 is a molecular weight of the bischloroformate compound when n=1 in the formula (1), the CF value (N/kg) is (CF number/concentration), the CF number (N) is a chlorine molecule number of the bischloroformate compound represented by the formula (1) contained in a 1 L reaction solution, the concentration (kg/L) is calculated from an amount of a solid resulting from condensation of the 1 L reaction solution, and 98.92 is a total atomic weight of two chlorine atoms, one oxygen atom and one carbon atom that exist outside n repeating units in the formula (1).

2. The method according to claim 1, wherein
the bischloroformate compound represented by the formula (1) is a bischloroformate compound represented by one of formulae (3) and (4) below, and
the dihydric phenol compound represented by the formula (2) is one of a biphenol compound represented by a formula (5) below and a bisphenol compound represented by a formula (6) below:

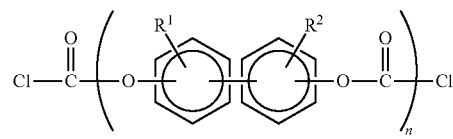

Formula (3)

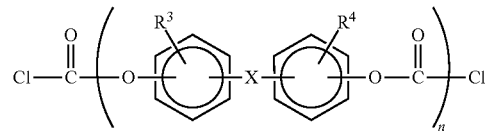

Formula (4)

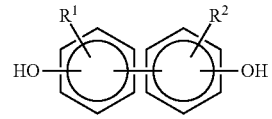

Formula (5)

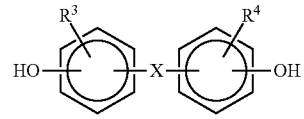

Formula (6)

where $R^1$ and $R^2$ each independently represent a hydrogen atom, an alkyl group having 1 to 12 carbon atoms, or a substituted or unsubstituted aryl group having 6 to 12 carbon atoms, $R^3$ and $R^4$ each independently represent a hydrogen atom, an alkyl group having 1 to 12 carbon atoms, an aryl group having 6 to 12 carbon atoms, or a halogen atom, and X is 9,9-fluorenylidene group, a divalent adamantyl group, or a linking group represented by one of formulae (7a) and (7b) below:

Formula (7a)

where $R^5$ and $R^6$ each independently a hydrogen atom, a trifluoromethyl group, an alkyl group having 1 to 12 carbon atoms, or an aryl group having 6 to 12 carbon atoms, and $R^5$ and $R^6$ may be combined with each other to provide a cycloalkylidene group having 4 to 12 carbon atoms;

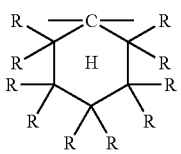

Formula (7b)

where each of a plurality of R is a hydrogen atom or an alkyl group having 1 to 3 carbon atoms, and at least one, preferably three, of the plurality of R is an alkyl group having 1 to 3 carbon atoms; and
substituents corresponding to $R^1$, $R^2$, $R^3$ and $R^4$ may be plurally combined with one benzene ring, and the combined substituents may be the same or different.

3. The method according to claim 1, further comprising:
suspending or dissolving the dihydric phenol compound represented by the formula (2) in the hydrophobic organic solvent;
introducing the phosgene compound into a resulting suspension or solution; and
dropping the aliphatic tertiary amine in a mixture obtained by the introducing of the phosgene compound, the aliphatic tertiary amine being diluted with the hydrophobic organic solvent.

4. The method according to claim 1, further comprising
suspending or dissolving the dihydric phenol compound represented by the formula (2) in the hydrophobic organic solvent;
introducing the aliphatic tertiary amine into a resulting suspension or solution; and
dropping the resulting suspension or solution, in which the aliphatic tertiary amine is introduced, in the phosgene compound being diluted with the hydrophobic organic solvent.

5. The method according to claim 1, wherein
a used amount of the aliphatic tertiary amine is 1.1 equivalent weight or less relative to a hydroxyl group in the dihydric phenol compound represented by the formula (2).

6. A polycarbonate oligomer having a small number of repeating units, the polycarbonate oligomer being produced using the bischloroformate compound that is obtained in the method according to claim 5 and is represented by the formula (1), the polycarbonate oligomer comprising a nitrogen-containing terminal group at a ratio of 10 mol % of all terminal groups or less or comprising no nitrogen-containing terminal group.

7. A bischloroformate compound production method of producing a bischloroformate compound represented by a formula (1) below, the method comprising:
continuously reacting a solution, in which a dihydric phenol compound represented by a formula (2) below is dissolved in an alkali aqueous solution, with a phosgene compound in a fine flow path in a micrometer order under presence of an inert organic solvent to obtain bischloroformate having an average number of repeating units (n) of 1.99 or less, the average number of repeating units (n) being calculated by an equation (1) below:

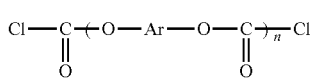

Formula (1)

Formula (2)

where Ar of the formulae (1) and (2) is a divalent aromatic group; and

Average Number of Repeating Units $(n)=1+(Mav-M1)/M2$   Equation (1)

where Mav is $(2\times 1000/(\text{CF value}))$, M2 is (M1−98.92), M1 is a molecular weight of the bischloroformate compound when n=1 in the formula (1), the CF value (N/kg) is (CF number/concentration), the CF number (N) is a chlorine molecule number of the bischloroformate compound represented by the formula (1) contained in a 1 L reaction solution, the concentration (kg/L) is calculated from an amount of a solid resulting from condensation of the 1 L reaction solution, and 98.92 is a total atomic weight of the two chlorine atoms, the one oxygen atom and the one carbon atom outside n repeating units in the formula (1).

8. The method according to claim 7, wherein
the bischloroformate compound represented by the formula (1) is a bischloroformate compound represented by one of formulae (3) and (4) below, and
the dihydric phenol compound represented by the formula (2) is one of a biphenol compound represented by a formula (5) below and a bisphenol compound represented by a formula (6) below:

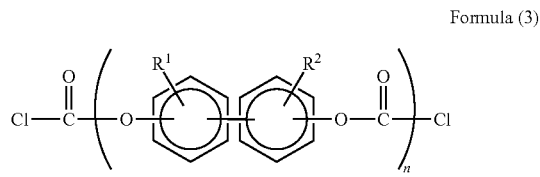

Formula (3)

Formula (4)

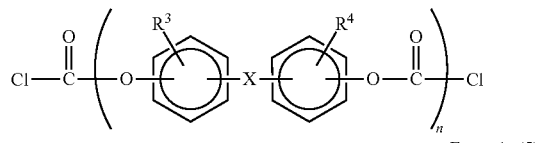

Formula (5)

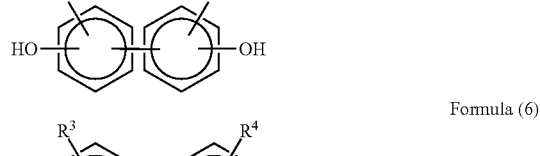

Formula (6)

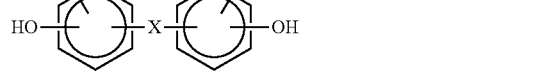

where $R^1$ and $R^2$ each independently represent a hydrogen atom, an alkyl group having 1 to 12 carbon atoms, or a substituted or unsubstituted aryl group having 6 to 12 carbon atoms, $R^3$ and $R^4$ each independently represent a hydrogen atom, an alkyl group having 1 to 12 carbon atoms, an aryl group having 6 to 12 carbon atoms, or a halogen atom, and X is 9,9-fluorenylidene group, a divalent adamantyl group, or a linking group represented by one of formulae (7a) and (7b) below:

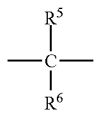

Formula (7a)

where $R^5$ and $R^6$ each independently a hydrogen atom, a trifluoromethyl group, an alkyl group having 1 to 12 carbon atoms, or an aryl group having 6 to 12 carbon atoms, and $R^5$ and $R^6$ may be combined with each other to provide a cycloalkylidene group having 4 to 12 carbon atoms;

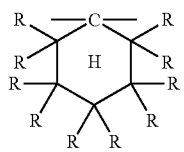

Formula (7b)

where each of a plurality of R is a hydrogen atom or an alkyl group having 1 to 3 carbon atoms, and at least one, preferably three, of the plurality of R is an alkyl group having 1 to 3 carbon atoms; and substituents corresponding to $R^1$, $R^2$, $R^3$ and $R^4$ may be plurally combined with one benzene ring, and the combined substituents may be the same or different.

9. The method according to claim 7, wherein
in the fine flow path, a linear velocity of a mixture of the dihydric phenol compound represented by the formula (2) and the phosgene compound falls within a range from 0.2 m/sec to 50 m/sec.

10. The method according to claim 7, wherein
in the fine flow path, a used amount of the phosgene compound falls within a range from 0.95 to 10 equivalent weight relative to a hydroxyl group of the dihydric phenol compound represented by the formula (2).

11. A bischloroformate-compound-containing solution comprising the bischloroformate compound produced in the method according to claim 1.

12. A bischloroformate-compound-containing solution comprising the bischloroformate compound produced in the method according to claim 7.

* * * * *